United States Patent [19]

Kakeya et al.

[11] Patent Number: 4,605,651
[45] Date of Patent: Aug. 12, 1986

[54] ANTIBIOTIC AMINO ACID DERIVATIVES OF CEPHALOSPORINS

[75] Inventors: Nobuharu Kakeya, Nagaokakyo; Susumu Nishizawa, Kyoto; Satoshi Tamaki, Moriyama; Kazuhiko Kitao, Kyoto, all of Japan

[73] Assignee: Kyoto Pharmaceutical Industries, Ltd., Kyoto, Japan

[21] Appl. No.: 540,676

[22] Filed: Oct. 11, 1983

[30] Foreign Application Priority Data

Nov. 10, 1982 [WO] PCT Int'l Appl. ... PCT/JP82/00437

[51] Int. Cl.$^4$ .................. A61K 31/545; C07D 501/36
[52] U.S. Cl. .................... 514/200; 514/204; 514/209; 540/215; 540/222; 540/223; 540/224; 540/226
[58] Field of Search ............... 424/246; 544/23, 26, 544/27, 16, 22, 24; 514/200, 204, 209

[56] References Cited

U.S. PATENT DOCUMENTS

| | | | |
|---|---|---|---|
| 3,701,775 | 10/1972 | Berges | 260/243 C |
| 3,812,116 | 5/1974 | Takano et al. | 544/26 |
| 4,041,161 | 9/1977 | Kocsis | 424/246 |
| 4,107,433 | 8/1978 | Bentley | 544/30 |

FOREIGN PATENT DOCUMENTS 1229453 4/1971 United Kingdom .
1328340 8/1973 United Kingdom .

*Primary Examiner*—Robert Gerstl
*Assistant Examiner*—Robert Benson
*Attorney, Agent, or Firm*—Berman, Aisenberg & Platt

[57] ABSTRACT

1. A cephalosporin derivatives of the general formula

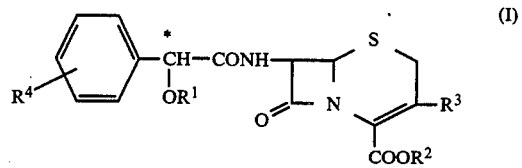

wherein $R^1$ is an $\alpha$-, $\beta$- or $\gamma$-amino acid residue (bonded by the ester linkage), which may optionally be substituted by one or two lower alkyl groups at the amino group thereof, $R^2$ is an 1-alkanoyloxyalkyl, 1-alkoxycarbonyloxyalkyl, phthalidyl or 5-methyl-1,3-dioxolen-2-on-4-ylmethyl group, $R^3$ is a carbamoyloxymethyl group, which may optionally be substituted by one or two lower alkyl groups, or a heterocyclothiomethyl group, which may optionally be substituted by one or more appropriate substituents, and $R^4$ is a hydrogen atom or a hydroxy group, or its non-toxic salt are found to be useful as orally administrable antibiotics having broad antimicrobial activities against both gram-positive and gram-negative bacteria.

20 Claims, No Drawings

ANTIBIOTIC AMINO ACID DERIVATIVES OF CEPHALOSPORINS

TECHNICAL FIELD AND DISCLOSURE OF INVENTION

This invention relates to cephalosporin derivatives represented by the general formula

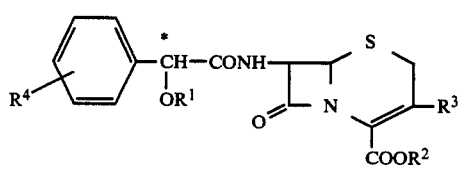

wherein $R^1$ is an α-, β- or γ-amino acid residue (bonded by the ester linkage), which may optionally be substituted by one or two lower alkyl groups at the amino group thereof, $R^2$ is an 1-alkanoyloxyalkyl, 1-alkoxycarbonyloxyalkyl, phthalidyl or 5-methyl-1,3-dioxolen-2-on-4-ylmethyl group, $R^3$ is a carbamoyloxymethyl group, which may optionally be substituted by one or two lower alkyl groups, or a heterocyclothiomethyl group, which may optionally be substituted by one or more appropriate substituents, and $R^4$ is a hydrogen atom or a hydroxy group, and nontoxic salts thereof; methods of producing the same; and prophylactic and therapeutic agents aganst bacterial infection which comprises the same as active ingredients.

As a result of intensive research in search of orally administrable cephalosporin derivatives, the present inventors have found that the above-mentioned novel cephalosporin derivatives (I) are satisfactory in absorbability through the digestive tract and can rapidly be hydrolyzed in vivo under the action of enzymes, whereby the carboxylate ester moiety at the 4-position of the cephem ring structure and the amino ester moiety at the α-position of the side chain at position 7 are hydrolyzed and the cephalosporin derivatives (I) are thereby converted to the corresponding unesterified species represented by the general formula

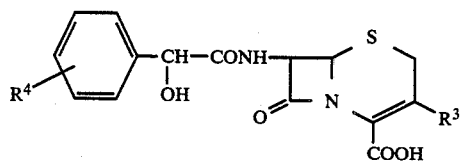

wherein $R^3$ and $R^4$ are as defined above; that, in other words, oral administration of cephalosporin derivatives (I) results in high blood levels of those unesterified species that have an excellent bacterial activity and said high blood levels can be retained for a prolonged period of time; that conversion of cephalosporin derivatives (I) into acid addition salts thereof results in improved absorbability and at the same time in stabilization of cephalosporin derivatives (I) and facilitation of the isolation procedure and of the production of pharmaceutical preparations for oral administration; and further that when cephalosporin derivatives (I) are administered orally in the presence of organic acids, the solubility of cephalosporin derivatives (I) is markedly increased and thereby the absorbability of cephalosporin derivatives (I) is further increased. At the same time, the present inventors have established the methods of producing cephalosporin derivatives (I), and thus have completed the present invention.

Accordingly, it is a primary object of the invention to provide novel cephalosporin derivatives which are orally administrable and have high antibacterial activity.

Another object of the invention is to provide methods of producing the above cephalosporin derivatives.

A third object of the invention is to provide orally administrable pharmaceutical compositions for prevention or treatment of bacterial infection.

Referring to general formula (I), the amino acid residue represented by $R^1$ is an α-, β- or γ-amino acid residue which, together with the adjacent oxygen atom, forms an ester bonding. Said amino acid residue may be substituted, on the amino group thereof, by one or two lower alkyl groups, preferably each containing 1 to 4 carbon atoms, such as methyl, ethyl, propyl, isopropyl or butyl. Such amino acid residue may be in the D, L or DL form, and furthermore it may be a peptide residue comprising two or more amino acids. The following are examples of such amino acid residue:

Neutral amino acid residues:
Aliphatic amino acid residues [glycyl, alanyl, valyl, leucyl, isoleucyl, etc.], hydroxyamino acid residues [seryl, threonyl, etc.], sulfur-containing amino acid residues [cysteinyl, cystinyl, methionyl, etc.], amidoamino acid residues [asparaginyl, glutaminyl, etc.], and aromatic amino acid residues [phenylalanyl, thyrosyl, tryptophyl, etc.];

Acidic amino acid residues:
Aspartyl, glutamyl, etc.;

Basic amino acid residues:
Histidyl, lysyl, arginyl, etc.;

Imino acid residues:
Prolyl, hydroxypropyl, etc.;

Other amino acid residues than α-amino acid residues:
β-Alanyl, γ-aminobutyryl, etc.;

N-Substituted amino acid residues:
Sarcosyl, N,N-dimethylglycyl, etc.;

Peptide residues:
Glycylglycyl.

Referring to $R^2$ in general formula (I), the alkanoyl moiety of the 1-alkanoyloxyalkyl group contains preferably 1 to 10 carbon atoms, more preferably 1 to 7 carbon atoms, while the alkyl moiety contains preferably 1 to 3 carbon atoms, more preferably 1 or 2 carbon atoms. Examples of such $R^2$ group are acetoxymethyl, propionyloxymethyl, iso-propionyloxymethyl, n-butyryloxymethyl, isobutyryloxymethyl, pivaloyloxymethyl, n-valeryloxymethyl, 2-methylbutyryloxymethyl, iso-valeryloxymethyl, n-hexanoyloxymethyl, 3-methylvaleryloxymethyl, neohexanoyloxymethyl, 2-methylhexanoyloxymethyl, 2,2-dimethylbutyryloxymethyl, diethylacetoxymethyl, dipropylacetoxmethyl, 2,2-dimethylvaleryloxymethyl, neoheptanoyloxymethyl, cyclohexanecarbonyloxymethyl, cyclohexylacetoxymethyl, 1-acetoxyethyl, 1-n-propionyloxyethyl, 1-n-butyryloxyethyl, 1-isobutyryloxyethyl, 1-n-valeryloxyethyl, 1-pivaloyloxyethyl, 1-isovaleryloxyethyl, 1-n-hexanoyloxyethyl and 1-cyclohexanecarbonyloxyethyl.

The alkoxy moiety of the alkoxycarbonyloxyalkyl group represented by $R^2$ contains preferably 1 to 10 carbon atoms, more preferably 1 to 7 carbon atoms, and the alkyl moiety contains preferably 1 to 3 carbon atoms, more preferably 1 or 2 carbon atoms. Examples of such group $R^2$ are 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, 1-tert-butoxycarbonyloxyethyl, 1-pentyloxycarbonyloxyethyl and 1-hexyloxycarbonyloxyethyl.

Preferred $R^2$ groups are acetoxymethyl, propionyloxymethyl, n-butyryloxymethyl, isovaleryloxymethyl, pivaloyloxymethyl, 1-acetoxyethyl, 1-propionyloxyethyl, 1-isobutyryloxyethyl, 1-n-valeryloxyethyl, 1-isovaleryloxyethyl, 1-pivaloyloxyethyl, phthalidyl, 1-ethoxycarbonyloxyethyl and 5-methyl-1,3-dioxolen-2-on-4-ylmethyl.

In the optionally lower alkyl-substituted carbamoyloxymethyl group represented by $R^3$, the lower alkyl group includes those containing 1 to 4 carbon atoms, such as methyl, ethyl, n-propyl, isopropyl and n-butyl.

The heterocycle moiety of the heterocycloethiomethyl group represented by $R^3$, which may be substituted by one or more appropriate substituents includes, within the meaning thereof, saturated or unsaturated, monocyclic or polycyclic heterocycles containing one or more hetero atoms (e.g. oxygen atom, sulfur atom, nitrogen atom), such as nitrogen-containing unsaturated monocyclic heterocycles [e.g. pyrrolyl, pyrrolinyl, imidazolyl, pyrazolyl, pyridyl or N-oxide thereof, pyrimidyl, pyrazinyl, pyridazinyl, triazolyl (4H-1,2,4-triazolyl, 1H-1,2,3-triazolyl, 2H-1,2,3-triazolyl, etc.), tetrazolyl (1H-tetrazolyl, 2H-tetrazolyl, etc.)], nitrogen-containing saturated monocyclic heterocycles [e.g. pyrrolidinyl, imidazolidinyl, piperidino, piperazinyl], nitrogen-containing unsaturated condensed heterocycles [e.g. indolyl, isoindolyl, indolidinyl, benzimidazolyl, quinolyl, isoquinolyl, indazolyl, benzotriazolyl], oxygen- and nitrogen-containing unsaturated monocyclic heterocycles [e.g. oxazolyl, isoxazolyl, oxadiazolyl (1,2,4-oxadiazolyl, 1,3,4-oxadiazolyl, 1,2,5-oxadiazolyl, etc.)], oxygen- and nitrogen-containing saturated monocyclic heterocycles [e.g. morpholinyl], oxygen- and nitrogen-containing unsaturated condensed heterocycles [e.g. benzoxazolyl, benzoxadiazolyl], sulfur- and nitrogen-containing unsaturated monocyclic heterocycles (e.g. thiazolyl, thiadiazolyl (1,2,3-thiadiazolyl, 1,2,4-thiadiazolyl, 1,3,4-thiadiazolyl, 1,2,5-thiadiazolyl, etc.)], sulfur- and nitrogen-containing saturated monocyclic heterocycles [e.g. thiazolidinyl], sulfur-containing unsaturated monocyclic heterocycles [e.g. thienyl] and sulfur- and nitrogen-containing unsaturated condensed heterocycles [e.g. benzothiazolyl, benzothiadiazolyl, etc.]. These heterocycles may have one or more appropriate substituents, such as alkyl and cycloalkyl groups (e.g. methyl, ethyl, propyl, isopropyl, butyl, isobutyl, pentyl, cyclopentyl, hexyl, cyclohexyl), preferably straight-chain or branched-chain alkyls of 1 to 6 carbon atoms (more preferably 1 to 4 carbon atoms) and cycloalkyls of 5 or 6 carbon atoms, alkenyl groups (e.g. vinyl, allyl, butenyl), aryl groups (e.g. phenyl, tolyl), halogens inclusive of chlorine, bromine, iodine and fluorine, and an amino group.

Particularly preferred examples of $R^3$ are carbamoyloxymethyl, (1,2,3-triazol-5-yl)thiomethyl, (1,3,4-oxadiazol-2-yl)thiomethyl, (1,3,4-thiadiazol-2-yl)thiomethyl, (5-methyl-1,3,4-thiadiazol-2-yl)thiomethyl, (1-methyl-1H-tetrazol-5-yl)thiomethyl and (2,5-dihydro-6-hydroxy-2-methyl-5-oxo-as-triazin-3-yl)thiomethyl, amongst others.

Cephalosporin derivatives (I) are preferably in the form of non-toxic salts, more preferably acid addition salts on the part of the amino acid residue thereof. Any pharmaceutically acceptable acids which can form salts with the amino acid residue moiety may be used as acids for forming said acid addition salts. Examples of such acids are mineral acids, such as hydrochloric acid, sulfuric acid, phosphoric acid and nitric acid, and organic acids, such as oxalic acid, fumaric acid, maleic acid, citric acid, tartaric acid, methanesulfonic acid and toluenesulfonic acid.

Cephalosporin derivatives (I) are preferably in the D configuration with respect to the carbon atom marked with an asterisk (*) in general formula (I).

Cephalosporin derivatives (I) in accordance with the present invention are produced, for example, in the following manner:

PROCESS 1

This process comprises reacting a compound of the general formula

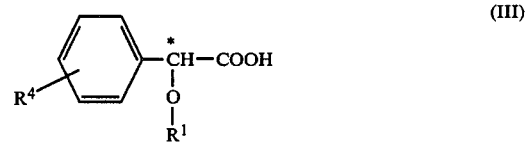
(III)

wherein $R^1$ and $R^4$ are as defined above, with a compound of the general formula

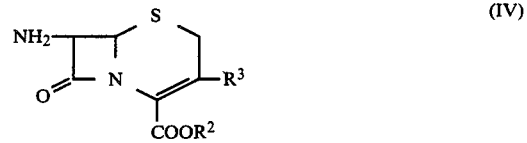
(IV)

wherein $R^2$ and $R^3$ are as defined above.

Compound (III) is used for said reaction in the form of free carboxylic acid or in the form of a reactive derivative thereof. Thus, it is subjected to the above acylation reaction as it is (i.e. as free acid) or in the form of a reactive derivative, such as a salt (e.g. sodium, potassium, calcium, triethylamine or pyridine salt), an acid halide (e.g. acid chloride, acid bromide), an acid anhydride, a mixed acid anhydride [e.g. anhydride with a substituted phosphoric acid (dialkylphosphoric acid, etc.) or an alkylcarbonic acid (monoethylcarbonic acid, etc.)], an active amide (e.g. amide with imidazole, etc.) or an ester (e.g. cyanomethyl ester, 4-nitrophenyl ester).

When compound (III) is used in the free acid or salt form, an adequate condensing agent is preferably used. Said condensing agent includes dehydrating agents, such as N,N'-disubstituted carbodiimides (e.g. N,N'-dicyclohexylcarbodiimide) and azolide compounds (e.g. N,N'-carbonyldiimidazole, N,N'-thionyldiimidazole). When such condensing agent is used, the reaction presumably proceeds via a reactive derivative of the carboxylic acid.

When, in compound (III) to be subjected to the above reaction, the amino group of the amino acid residue represented by $R^1$ is a primary or secondary amino group, said amino group is preferably protected with an amino-protecting group, such as 2,2,2-trichloroethoxycarbonyl, 2-methylsulfonylethyloxycarbonyl, tert-butoxycarbonyl (hereinafter sometimes referred to as BOC), chloroacetyl or trityl.

The above reaction is generally carried out in an inert solvent. Examples of the solvent are water, acetone, dioxane, acetonitrile, chloroform, benzene, methylene chloride, ethylene chloride, tetrahydrofuran, ethyl acetate, N,N-di-methylformamide, pyridine and the like organic solvents and mixtures of these.

The reaction is preferably carried out at room temperature or under cooling (−20° C. to 0° C.).

Compound (IV) is produced, for example, by reacting a compound of the general formula

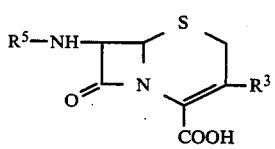

wherein $R^3$ is as defined above and $R^5$ is a hydrogen atom or an amino-protecting group, with a compound of the general formula $$X—R^2 \quad (VI)$$

wherein $R^2$ is as defined above and X is a group reactive with the carboxyl group (or a reactive group derived therefrom).

Referring to $R^5$ in general formula (V), the amino-protecting group is a per se known amino-protecting group, such as benzylcarbonyl, 2-thienylacetyl, 2-furylacetyl, D-5-amino-5-carboxyvaleryl, trityl or phthalimido.

Referring to general formula (VI), the group reactive with the carboxyl group (or a reactive group derived therefrom) as represented by X is, for example, a halogen atom (bromine, chlorine, iodine, etc.), an alkylsulfonyloxy group (methanesulfonyloxy, etc.) or an arylsulfonyloxy group (p-toluenesulfonyloxy, etc.).

In carrying out the above reaction, compound (V) is preferably used as a reactive derivative thereof (e.g. an alkali metal salt, such as sodium or potassium salt, and alkaline earth metal salt, such as calcium salt, triethylamine salt, pyridine salt).

The reaction is preferably carried out under cooling so that formation of byproduct $\Delta^2$-isomers can be avoided. The presence of a solvent which does not interfere with the reaction (e.g. dimethylformamide, dimethylacetamide, hexamethylphosphorictriamide, acetone, acetonitrile) can contribute to smooth progress of the reaction.

In carrying out the reaction, it is preferable that $R^5$ in general formula (V) is an amino-protecting group. In that case, the reaction of compound (V) and compound (VI) gives those species of compound (IV) in which, i.e. in general formula (IV), the amino group at position 7 is protected. The protective group can be eliminated by the per se known method of deprotection.

More concretely, the means for eliminating said protective group includes iminochlorination with phosphorus pentachloride followed by methanolysis, for instance, for the removal of benzylcarbonyl, 2-thienylacetyl, 2-furylacetyl, D-5-amino-5-carboxyvaleryl, etc., treatment with an acid (e.g. formic acid, trifluoroacetic acid), for instance, for the removal of trityl, etc., and the Ing-Manske's method using hydrazine, for instance, for the removal of phthalimido, etc.

PROCESS 2

This process comprises reacting a compound of the general formula

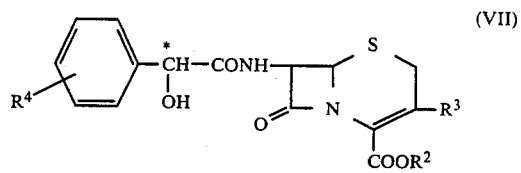

wherein $R^2$, $R^3$ and $R^4$ are as defined above, with a compound of the general formula $$R^1OH \quad (VIII)$$

wherein $R^1$ is as defined above.

Compound (VIII) is subjected to the above reaction in the form of free carboxylic acid or as a reactive derivative derived therefrom. Thus, it is subjected to the acylation reaction in the free acid form or in the form of a reactive derivative thereof, such as a salt (e.g. sodium, pottasium, calcium, triethyalmine or pyridine salt), an acid halide (acid chloride, acid bromide, etc.), an acid anhydride, a mixed acid anhydride [anhydride with a substituted phosphoric acid (dialkylphosphoric acid, etc.), an alkylcarbonic acid (monoethylcarbonic acid, etc.), etc.], an active amide (e.g. amide with imidazole) or an ester (e.g. cyanomethyl ester, 4-nitrophenyl ester).

When compound (VIII) is used in the free acid or salt form, an appropriate condensing agent is preferably used. The condensing agent, includes, among ethers, dehydrating agents such as N,N'-disubstituted carbodiimides (e.g. N,N'-dicyclohexylcarbodiimide) and azolide compounds (e.g. N,N'-carbonyldiimidazole, N,N'-thionyldiimidazole). In cases where such condensing agent is used, the reaction presumably proceeds via a reactive derivative of the carboxylic acid. In carrying out the reaction, the use of a base, such as 4-dimethylaminopyridine, as the catalyst is preferred.

When the amino group in compound (VIII) to be subjected to the above reaction is primary or secondary, said amino group is preferably protected with a protective group, for example 2,2,2-trichloroethoxycarbonyl, 2-methylsulfonylethyloxycarbonyl, tert-butoxycarbonyl, chloroacetyl or trityl.

The reaction is generally carried out in an inert solvent. The solvent includes water, acetone, dioxane, acetonitrile, chloroform, benzene, methylene chloride, ethylene chloride, tetrahydrofuran, ethyl acetate, N,N-dimethylformamide, pyridine and other organic solvents, and mixtures thereof.

Compound (VII) is produced by reacting compound (II) with compound (VI).

Compound (VII) is preferably subjected to the reaction as a reactive derivative thereof (e.g. an alkali metal salt, such as sodium salt or potassium salt, an alkaline earth metal salt, such as calcium salt, triethylamine salt, pyridine salt).

This reaction is preferably carried out under cooling so that formation of byproduct $\Delta^2$-isomers can be avoided. Said reaction can proceed smoothly in the presence of a solvent which does not interfere with the reaction (e.g. dimethylformamide, dimethylacetamide, hexamethylphoricttriamide, acetone, acetonitrile, dimethyl sulfoxide).

PROCESS 3

This process comprises reacting a compound of the general formula

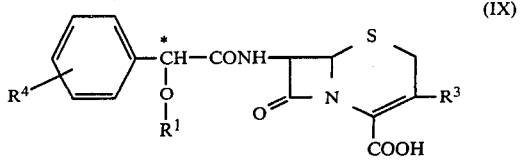

wherein $R^1$, $R^3$ and $R^4$ are as defined above, with compound (VI).

Compound (IX) is preferably subjected to the above reaction as a reactive derivative thereof (e.g. an alkali metal salt, such as sodium salt or potassium salt, an alkaline earth metal salt, such as calcium salt, triethylamine salt, pyridine salt).

This reaction is preferably carried out under cooling so that formation of byproduct $\Delta^2$-isomers can be avoided. Said reaction can proceed smoothly in the presence of a solvent which does not interfere with the reaction (e.g. dimethylformamide, dimethylacetamide, hexamethylphosphorictriamide, acetone, acetonitrile).

When, in carrying out the above reaction, the amino group of $R^1$ in general formula (IX) is primary or secondary, the amino group is preferably protected. In that case, the reaction of compound (IX) with compound (VI) gives those species of compound (I) in which $R^1$ in general formula (I) is a protected amino group. The protective group, however, can be eliminated by the per se known method of deprotection.

Cephalosporin derivatives (I) can be converted to their salts with the per se known method.

Cephalosporin derivatives (I) and salts thereof can be isolated and purified by the conventional method.

By diluting the thus-produced cephalosporin derivatives (I) or salts thereof with excipients for pharmaceutical use by the per se known means, there can be produced orally administrable pharmaceutical preparations for preventing and treating bacterial infection. The dilution is performed by the per se known means, such as mixing. The excipients are, for example, starch, lactose, sucrose, calcium carbonate and calcium phosphate.

It is preferable to further add an organic acid to said orally administrable pharmaceutical preparations for the prevention and treatment of bacterial infection. In this manner, the dissolution of cephalosporin derivatives (I) in the digestive tract is promoted, hence the absorption thereof into the blood is facilitated. Any pharmaceutically acceptable organic acids may be used without any particular restriction. Thus, for instance, organic carboxylic acids, such as maleic acid, fumaric acid, tartaric acid, citric acid, succinic acid, malic acid, oxalic acid, mandelic acid, malonic acid and benzoic acid, are preferably used. The level of addition of such organic acids is generally 0.01 to 20 moles, preferably 0.02 to 2 moles, per mole of cephalosporin derivative (I) or a salt thereof.

If desired, other additives may be further added to said orally administrable pharmaceutical preparations for the prevention and treatment of bacterial infection. Preferred additives are, for instance, binders (e.g. starch, gum arabic, carboxymethylcellulose, hydroxypropylcellulose, crystalline cellulose), lubricants (e.g. magnesium stearate, talc) and disintegration promoters (e.g. carboxymethylcellulose calcium, talc). After admixture of necessary components, the mixture can be made into dosage forms suited for oral administration, such as capsules, tablets, fine granules, granules and dry syrup, by the per se known means.

Oral administration of the pharmaceutical preparations for the prevention and treatment of bacterial infection in accordance with the present invention results in rapid absorption of the active ingredients, namely cephalosporin derivatives (I) or salts thereof, through the digestive tract, immediately followed by in vivo hydrolysis by enzymes, whereby they are converted to the corresponding unesterified species or salts thereof.

The unesterified species and salts thereof have excellent antibacterial activity. Thus, they exhibit excellent activity against gram-positive bacteria, inclusive of *Staphylococcus aureus*, and gram-negative bacteria, inclusive of *Escherichia coli, Klebsiella pneumoniae, Proteus vulgaris, Proteus mirabilis* and *Proteus morganii*. In addition, the unesterified species and salts thereof have very low toxicity.

Therefore, the pharmaceutical preparations for the prevention and treatment of bacterial infection in accordance with the present invention can be used as the means for preventing or treating bacterial diseases (e.g. suppurative or purulent diseases, respiratory tract infection, biliary tract infection, urinary tract infection) in humans and other warm-blooded animals (e.g. dog, cat, cattle, horse, rat, mouse).

The dose of cephalosporin derivatives (I) and salts thereof depends on the subject to be treated therewith, the symptoms and other factors. In adult humans with suppurative or purulent diseases, for instance, they are administered orally, for example in a single dose of about 1 to 40 mg/kg of body weight as calculated as the corresponding unesterified species about 1 to 4 times daily.

EXAMPLE 1

Synthesis of pivaloyloxymethyl 7-[D-O-(glycyl)mandelamido]-3-[(1-methyl-1H-tetrazol-5-yl)thiomethyl]-3-cephem-4-carboxylate hydrochloride (Compound No. 333)

(i) BOC-glycine (1.65 g) is dissolved in 100 ml of methylene chloride and, then, 110 mg of 4-dimethylaminopyridine is added. With stirring at 0° C., 3 g of benzhydryl D-mandelate and 1.94 g of dicyclohexylcarbodiimide are added and the reaction is performed for 3 hours. Extraction with ethyl acetate and crystallization from petroleum ether give 1.8 g of benzhydryl O-(BOC-glycyl)mandelate.

NMR(CDCl$_3$, δ values); 1.43(s, 9H, —C(CH$_3$)$_3$) 4.02(d, 2H, J=6 Hz, —CH$_2$NH—), 5.05(t, 1H, J=6 Hz, —CH$_2$NH—), 6.10(s, 1H, —CHCO—), 6.82(s, 1H, —CH(C$_6$H$_5$)$_2$), 7.30(m, 15H, phenyl).

(ii) The compound obtained in (i) is dissolved in 30 ml of ethanol, then 300 mg of palladium oxide is added and catalytic reduction is conducted. Thereafter, the catalyst is filtered off, and the filtrate is concentrated and crystallized from petroleum ether to give 1.1 g of O-(BOC-glycyl)-mandelic acid.

NMR((CD$_3$)$_2$CO, δ values); 1.41(s, 9H, —C(CH$_3$)$_3$), 3.47 (d, 2H, J=6 Hz, —CH$_2$NH—), 5.94(s, 1H, —CHCO—), 6.25, 7.10 (br, 2H, —NH—, —CO$_2$H), 7.42(m, 5H, phenyl).

(iii) The compound obtained in (ii) (155 mg) is dissolved in 15 ml of methylene chloride, then 208 mg of dicyclohexylcarbodiimide is added at 0° C., the mixture is stirred for 10 minutes, 221 mg of pivaloyloxymethyl 7-amino-3-[(1-methyl-1H-tetrazol-5-yl)thiomethyl]-3-cephem-4-carboxylate is added and the reaction is conducted at the same temperature for 2 hours. The insoluble matter is filtered off, and the filtrate is washed with an aqueous sodium hydrogen carbonate solution and then with an aqueous sodium chloride solution, dried over anhydrous sodium sulfate and concentrated, and the residue is crystallized from isopropyl ether to give 320 mg of pivaloyloxymethyl 7-[D-O-(BOC-glycyl)mandelamido]-3-[(1-methyl-1H-tetrazol-5-yl)thiomethyl]-3-cephem-4-carboxylate.

IR(nujol, cm$^{-1}$); 3350, 1780, 1750, 1690.

NMR(CDCl$_3$, δ values); 1.22(s, 9H, (CH$_3$)$_3$CCO—), 1.42(s, 9H, (CH$_3$)$_3$CO—), 3.72(br, s. 2H, H$_2$ at position 2), 3.95(m, 5H, tetrazole —CH$_3$, CH$_2$NH—), 4.21, 4.55(d, d, 2H, J=14 Hz, —CH$_2$S— at position 3), 4.97(d, 1H, J=5 Hz, H at position 6), 5.00(br, 1H, —NH—), 5.68~6.0(m, 3H, —OCH$_2$O—, H at position 7), 6.18(s, 1H, —CHCONH—), 7.30(d, 1H, J=9 Hz, —CONH—), 7.42 (s, 5H, phenyl).

(iv) The compound obtained in (iii) is dissolved in 3 ml of dioxane. Thereto is added 2.5 ml of ethanolic 5N hydrochloric acid at room temperature, followed by stirring for 30 minutes. Addition of 30 ml of ether causes precipitation of crystals. The crystals are collected by centrifugal filtration to give 105 mg of the title compound.

IR(nujol, cm$^{-1}$); 3200, 1780, 1750, 1690.

NMR((CD$_3$)$_2$SO, δ values); 1.18(s, 9H, —C(CH$_3$)$_3$), 3.65(br, s, 2H, H$_2$ at position 2), 3.93(br, s, 5H, tetrazole —CH$_3$, —CH$_2$CO—), 4.15, 4.42(d, d, 2H, J=14 Hz, —CH$_2$S— at position 3), 5.02(d, 1H, J=5 Hz, H at position 6), 5.55~6.05(m, 3H, H at position 7, —OCH$_2$O—), 6.13(s, 1H,

—CHCONH—), 7.20~7.70(m, 5H, phenyl), 8.55(br, 3H, —NH$_3$$^+$), 9.45(d, 1H, J=9 Hz, —CONH—).

EXAMPLE 2

Synthesis of 1-acetoxyethyl 7-[D-O-(L-alanyl)mandelamido]-3-[(5-methyl-1,3,4-thiadiazol-2-yl)thiomethyl]-3-cephem-4-carboxylate hydrochloride (Compound No. 22)

(i) 1-Acetoxyethyl 7-(D-mandelamido)-3-[(5-methyl-1,3,4-thiadiazol-2-yl)thiomethyl]-3-cephem-4-carboxylate is dissolved in 30 ml of methylene chloride. Under ice cooling, 210 mg of BOC-alanine, 25 mg of 4-dimethylaminopyridine and 270 mg of dicyclohexylcarbodiimide are added, and the mixture is stirred for an hour. The insoluble matter is filtered off, and the filtrate is washed with 10% aqueous citric acid, aqueous sodium hydrogen carbonate and aqueous sodium chloride in that order and dried over anhydrous sodium sulfate. Removal of the solvent by distillation and the subsequent addition of petroleum ether to the residue give 110 mg of 1-acetoxyethyl 7-[D-O-(BOC-alanyl)mandelamido]-3-[(5-methyl-1,3,4-thiadiazol-2-yl)thiomethyl]-3-cephem-4-carboxylate as a slightly yellow powder.

IR(nujol, cm$^{-1}$); 3350, 1770, 1750, 1680.

NMR((CD$_3$)$_2$SO, δ values); 0.75~1.92(m, 15H, (CH$_3$)$_3$CO—, 2×CH$_3$CH—, 2.07(s, 3H, CH$_3$CO—), 2.68(s, 3H, thiadiazole —CH$_3$), 3.62(br, s, 2H, H$_2$ at position 2), 3.93~4.27(m, 1H,

—CHNH—), 4.14, 4.49, (d, d, 2H, J=14 Hz, —CH$_2$S— at position 3), 5.06(d, 1H, J=5 Hz, H at position 6), 5.35~5.95(m, 2H, H at position 7, BOC —NH—), 6.00(s, 1H, —CHCONH—), 6.82, 6.91(q, q, 1H, J=7 Hz,

—OCHO—), 7.40(s, 5H, phenyl), 9.28(d, 1H, J=9 Hz, —CONH—).

(ii) The compound obtained in (i) is dissolved in 6 ml of ethyl acetate. Thereto is added 5 ml of 2N hydrochloric acid in isopropyl alcohol, and the mixture is stirred at room temperature for an hour, followed by addition of 6 ml of ethyl acetate. The resultant white crystals are washed with ether to give 600 mg of the title compound.

IR(nujol, cm$^{-1}$); 1780, 1755, 1690.

NMR((CD$_3$)$_2$SO, δ values); 1.49(d, 6H, J=6 Hz, 2×CH$_3$CH—), 2.09(s, 3H, CH$_3$CO—), 2.70(s, 3H, thiadiazole —CH$_3$), 3.65 (br, s, 2H, H$_2$ at position 2), 4.15, 4.55(d, d, 2H, J=14 Hz, —CH$_2$S— at position 3), 4.8(m, 1H,

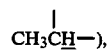
CH$_3$CH—), 5.08(d, 1H, J=5 Hz, H at position 6), 5.74(m, 1H, H at position 7), 6.12(s, 1H,

—CHCONH—), 6.93, 7.02(q, q, 1H, J=6 Hz,

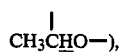
CH$_3$CHO—), 7.45(m, 5H, phenyl), 8.7(br, 3H, —NH$_3$$^+$), 9.45(d, 1H, J=9 Hz, —CONH—).

EXAMPLE 3

Synthesis of 1-ethoxycarbonyloxyethyl 7-[D-O-(L-alanyl)mandelamido]-3-[(1,3,4-thiadiazol-2-yl)thiomethyl]-3-cephem-4-carboxylate (Compound No. 237)

(i) BOC-L-alanine (1.89 g) is dissolved in 100 ml of methylene chloride and, then, 110 mg of 4-dimethylaminopyridine is added. With stirring at 0° C., 3.2 g of benzhydryl D-mandelate and 2.1 g of dicyclohexylcarbodiimide are added and the reaction is allowed to proceed for 3 hours. The insoluble matter is filtered off, the filtrate is concentrated, and the concentrate is extracted with ethyl acetate. Crystallization from petroleum ether gives 2.1 g of benzhydryl O-(BOC-L-alanyl)mandelate.

NMR(CDCl$_3$, δ values); 1.49(s, 9H, —C(CH$_3$)$_3$), 1.36(d, 3H, J=7 Hz, CH$_3$CH—), 4.45 (m, 1H, CH$_3$CH—) 5.02(d, 1H, J=7 Hz, —CHNH—), 6.11(s, 1H,

6.87(s, 1H, —CH(C$_6$H$_5$)$_2$), 7.35 (m, 15H, phenyl).

(ii) The compound obtained in (i) is dissolved in 30 ml of ethanol. Following addition of 300 mg of palladium oxide, catalytic reduction is conducted. There is thus obtained 1.2 g of (BOC-L-alanyl)-D-mandelic acid.
NMR((CD$_3$)$_2$SO, δ values); 1.40(s, 9H, —C(CH$_3$)$_3$), 1.35 (d, 3H, J=7 Hz,

4.43(m, 1H,

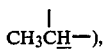

5.95(s, 1H, —CHCO$_2$H), 6.40, 7.10(br, 2H, —NH—, —CO$_2$H), 7.40(m, 5H, phenyl).

(iii) The compound obtained in (ii) is dissolved in 30 ml of anhydrous tetrahydrofuran, the solution is cooled to −20° C. in a nitrogen atmosphere, 4.8 ml of a 10% solution of triethylamine in tetrahydrofuran is added, followed by addition of a solution of 520 mg of ethyl chlorocarbonate in 2 ml of tetrahydrofuran, and the mixture is stirred at −20° C. for 30 minutes, Separately, 14 g of 7-amino-3-(1,3,4-thiadiazol-2-yl)thiomethyl-3-cephem-4-carboxylic acid is suspended in 30 ml of 50% aqueous tetrahydrofuran and, then, 4 ml of a 10% triethylamine solution in tetrahydrofuran is added, whereupon the suspension turns to a homogeneous solution. Thereto is added the previously prepared mixed acid anhydride solution at −20° C. The mixture is stirred at 0° C. for an hour and then at room temperature for an hour. Thereafter, the reaction mixture is adjusted to pH about 2 with phosphoric acid and then extracted with ethyl acetate. The extract is washed with aqueous sodium chloride and dried over anhydrous sodium sulfate. Removal of the solvent by distillation and addition of isopropyl ether give 1.3 g of 7-[D-O-(BOC-L-alanyl)mandelamido]-3-[(1,3,4-thiadiazol-2-yl)thiomethyl]-3-cephem-4-carboxylic acid.
NMR((CD$_3$)$_2$SO, δ values); 1.40(s, 9H, C(CH$_3$)$_3$), 1.45(d, 3H, J=7 Hz,

3.60(br, s, 2H, H$_2$ at position 2), 4.40(m, 1H,

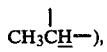

4.16, 4.53(d, d, 2H, J=14 Hz, —CH$_2$S— at position 3), 5.02(d, 1H, J=5 Hz, H at position 6), 5.10 (br, s, 1H, —NH—), 5.55~5.85(m, 1H, H at position 7), 6.04 (s, 1H,

7.42(br, s, 5H, phenyl), 7.30(br, 1H, —CO$_2$H), 9.35(d, 1H, J=9 Hz, —CONH—), 9.50(s, 1H, H at position 5 of thiadiazole).

(iv) The compound obtained in (iii) (1 g) and 160 mg of potassium acetate are dissolved in 20 ml of dimethylacetamide. Thereto is added 450 mg of 1-iododiethyl carbonate at −15° C., and the mixture is stirred at the same temperature for an hour. Ethyl acetate is added, and the whole mixture is washed with aqueous sodium hydrogen carbonate and then with aqueous sodium chloride and dried over anhydrous sodium sulfate. The solvent is then distilled off under reduced pressure. Addition of isopropyl ether gives 1.05 g of 1-ethoxycarbonyloxyethyl 7-[D-O-(BOC-L-alanyl)-mandelamido]-3-[(1,3,4-thiadiazol-2-yl)thiomethyl]-3-cephem-4-carboxylate as crystals.
IR(nujol, cm$^{-1}$); 3320, 1780, 1750, 1680.
NMR(CDCl$_3$, δ values); 1.32(t, 3H, J=7 Hz, CH$_3$CH$_2$O—), 1.41 (s, 9H, ((CH$_3$)$_3$C—), 1.41(d, 3H, J=7 Hz,

1.60, 1.62 (d, d, 3H, J=7 Hz,

3.70(br, s, 2H, H$_2$ at position 2), 4.05~4.80(m, 5H, —OCH$_2$CH$_3$,

CH$_2$S— at position 3), 4.98, 5.00(d, d, J=5 Hz, H at position 6), 5.20(br, 1H, —NH—), 5.60~5.90(m, 1H, H at position 7), 6.20(s, 1H,

6.93, 7.02(q, q, 1H, J=7 Hz,

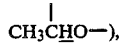

7.40(m, 6H, phenyl, —CONH—), 9.55(s, 1H, H at position 5 of thiadiazole).

(v) The compound obtained in (iv) (430 mg) is dissolved in 4 ml of dioxane. Thereto is added 3 ml of 5N ethanolic hydrochloric acid, and the mixture is stirred at room temperature for 80 minutes. Ethyl acetate (80 ml) is added, and the resulting crystalline precipitate is washed with ether to give 320 mg of the title compound.
IR(nujol, cm$^{-1}$); 1785, 1760, 1695.

NMR((CD$_3$)$_2$SO, δ values); 1.23(t, 3H, J=7 Hz, CH$_3$CH$_2$—), 1.49(d, 3H, J=7 Hz,

CH$_3$CHCO—), 1.51(d, 3H, J=7 Hz,

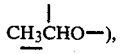
CH$_3$CHO—), 3.65(br, s, 2H, H$_2$ at position 2), 3.88~4.25(m, 5H, —CH$_2$S— at position 3, CH$_3$CH$_2$O—,

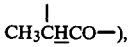
CH$_3$CHCO—), 5.05, 5.08(d, d, 1H, J=5 Hz, H at position 6), 5.54~5.90(m, 1H, H at position 7), 6.12(s, 1H,

—CHCONH—), 6.83, 6.91(q, q, 1H, J=7 Hz,

CH$_3$CHO—), 7.45(m, 5H, phenyl), 8.65(br, 3H, —NH$_3$+), 9.45(d, 1H, J=9 Hz, —CONH—), 9.54(s, 1H, H at position 5 of thiadiazole).

EXAMPLE 4 TO 26

By following the procedure of Example 2, there are produced the compounds specified below:

Acetoxymethyl 7-[D-O-(L-alanyl)mandelamido]-3-[(5-methyl-1,3,4-thiadiazol-2-yl)thiomethyl]-3-cephem-4-carboxylate hydrochloride (Compound No. 15) [Example 4]

IR(nujol, cm$^{-1}$); 1780, 1760, 1690.
NMR((CD$_3$)$_2$SO, δ values); 1.46(d, 3H, J=7 Hz,

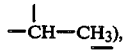
—CH—CH$_3$), 2.08(s, 3H, —CO—CH$_3$), 2.68(s, 3H, thiadiazole —CH$_3$), 3.65 (br, s, 2H, H$_2$ at position 2), 4.20(m, 1H, —CH—CH$_3$), 4.17, 4.58(d, d, J=14 Hz, 2H, —CH$_2$S— at position 3), 5.05(d, 1H, J=5 Hz, H at position 6), 5.77(d×d, 1H, J=5 and 9 Hz, H at position 7), 5.74 and 5.88(d, 2H, J=7 Hz, —CH$_2$OCO—), 6.12(s, 1H,

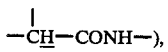
—CH—CONH—), 7.45(m, 5H, phenyl), 8.62(br, 3H, —NH$_3$+), 9.45 (d, 1H, J=9 Hz, —CONH—).

Pivaloyloxymethyl 7-[D-O-(L-alanyl)mandelamido]-3-[(5-methyl-1,3,4-thiadiazol-2-yl)thiomethyl]-3-cephem-4-carboxylate hydrochloride (Compound No. 25) [Example 5]

IR(nujol, cm$^{-1}$); 1785, 1755, 1690.
NMR((CD$_3$)$_2$SO, δ values); 1.16(s, 9H, —CH$_3$×3), 1.48(d, 3H, J=8 Hz,

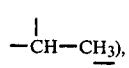
—CH—CH$_3$), 2.68(s, 3H, thiadiazole —CH$_3$), 3.64 (br, s, 2H, H$_2$ at position 2), 4.20(m, 1H,

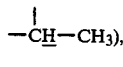
—CH—CH$_3$), 4.12 and 4.57(d, d, 2H, J=14 Hz, —CH$_2$—S— at position 3), 5.04 (d, 1H, J=5 Hz, H at position 6), 5.77(d, d, 1H, J=5 and 9 Hz, H at position 7), 5.74 and 5.95(d, d, 2H, J=7 Hz, —CH$_2$—OCO—), 6.12(s, 1H,

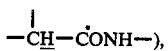
—CH—CONH—), 7.13(m, 5H, phenyl), 8.63(br, 3H, —NH$_3$+), 9.45(d, 1H, J=9 Hz, —CONH—).

Pivaloyloxymethyl 7-[D-O-(L-valyl)mandelamido]-3-[(5-methyl-1,3,4-thiadiazol-2-yl)thiomethyl]-3-cephem-4-carboxylate hydrochloride (Compound No. 39) [Example 6]

IR(nujol, cm$^{-1}$); 3200, 1780, 1750, 1690.
NMR((CD$_3$)$_2$SO, δ values); 0.96(d, 6H, J=7 Hz, —CH(CH$_3$)$_2$), 1.18 (s, 9H, —C(CH$_3$)$_3$), 2.30(m, 1H, —CH(CH$_3$)$_2$), 2.68(s, 3H, thiadiazole —CH$_3$), 3.65(br, s, 2H, H$_2$ at position 2), 4.11 and 4.57(d, d, 2H, J=14 Hz, —CH$_2$—S— at position 3), 4.10(m, 1H,

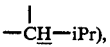
—CH—iPr), 5.05(d, 1H, J=5 Hz, H at position 6), 5.60~6.05(m, 3H, H at position 7, —COOCH$_2$—), 6.15(s, 1H,

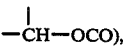
—CH—OCO), 7.25~7.70(m, 5H, phenyl), 8.63(br, 3H, —NH$_3$+), 9.45(d, 1H, J=9 Hz, —CONH—).

Pivaloyloxymethyl 7-[D-O-(L-prolyl)mandelamido]-3-[(5-methyl-1,3,4-thiadiazol-2-yl)thiomethyl]-3-cephem-4-carboxylate hydrochloride (Compound No. 151) [Example 7]

IR(nujol, cm$^{-1}$); 1780, 1750, 1685
NMR((CD$_3$)$_2$SO, δ values); 1.16 (s, 9H, —C(CH$_3$)$_3$), 1.70~2.40(m, 4H, H$_2$ at positions 3 and 4 of proline), 2.68(s, 3H, thiadiazole —CH$_3$), 3.05~3.45(m, 2H, H$_2$ at position 5 of proline), 3.64(br, s, 2H, H$_2$ at position 2), 4.10 and 4.55 (d, d, 2H, J=14 Hz, —CH$_2$S— at position 3), 4.35~4.53(m, 1H, H at position 2 of proline), 5.05(d, 1H, J=5 Hz, H at position 6), 5.55~6.05(m, 3H, H at position 7, —CO$_2$CH$_2$—), 6.15(s, 1H,

—CHCONH—), 7.43(m, 5H, phenyl), 9.30(br, 2H,

9.40(d, 1H, J=9 Hz, —CONH—).

Pivaloyloxymethyl 7-[D-O-(sarcosyl)mandelamido]-3-[(5-methyl-1,3,4-thiadiazol-2-yl)thiomethyl]-3-cephem-4-carboxylate hydrochloride (Compound No. 179) [Example 8]

IR(nujol, cm$^{-1}$); 3200, 1780, 1750, 1690.

NMR((CD$_3$)$_2$SO, δ values); 1.17(s, 9H, —C(CH$_3$)$_3$), 2.60 (s, 3H, —NHCH$_3$), 2.68(s, 3H, thiadiazole —CH$_3$), 3.65(br, s, 2H, H$_2$ at position 2), 4.12(br, s, 2H, —COCH$_2$—), 4.14, 4.55 (d, d, 2H, J=14 Hz, —CH$_2$S— at position 3), 5.05(d, 1H, J=5 Hz, H at position 6), 5.60~6.05(m, 3H, H at position 7, —CO$_2$CH$_2$—), 6.15(s, 1H,

7.25~7.75(m, 5H, phenyl), 9.50(m, 3H, —CONH,

(5-Methyl-1,3-dioxolen-2-on-4-ylmethyl) 7-[D-O-(L-alanyl)mandelamido]-3-[(5-methyl-1,3,4-thiadiazol-2-yl)thiomethyl]-3-cephem-4-carboxylate hydrochloride (Compound No. 28) [Example 9]

IR(nujol, cm$^{-1}$); 1815, 1780, 1690.

NMR((CD$_3$)$_2$SO, δ values); 1.48(d, 3H, J=7 Hz,

2.18 (s, 3H, dioxolene —CH$_3$), 2.66(s, 3H, thiadiazole —CH$_3$), 3.62 (br, s, 2H, H$_2$ at position 2), 4.20(m, 1H,

4.07, 4.65(d, d, 2H, J=14 Hz, —CH$_2$S— at position 3), 5.05(d, 1H, J=5 Hz, H at position 6), 5.15(s, 2H, —CO$_2$CH$_2$—), 5.72(d×d 1H, J=5 and 9 Hz, H at position 7), 6.13(s, 1H,

7.63(m, 5H, phenyl), 8.73(br, 3H, —NH$_3$+), 9.46(d, 1H, J=9 Hz, —CONH—).

(5-Methyl-1,3-dioxolen-2-on-4-ylmethyl) 7-[D-O-(L-prolyl)-mandelamido]-3-[(5-methyl-1,3,4-thiadiazol-2-yl)thiomethyl]-3-cephem-4-carboxylate hydrochloride (Compound No. 154) [Example 10]

IR(nujol, cm$^{-1}$); 1820, 1785, 1740, 1680.

NMR((CD$_3$)$_2$SO, δ values); 1.7~2.4(m, 7H, H$_2$ at positions 3 and 4 of proline, dioxolene —CH$_3$), 2.70(s, 3H, thiadiazole —CH$_3$), 3.05~3.4(m, 2H, H$_2$ at position 5 of proline), 3.59, 3.97(d, d, 2H, J=18 Hz, H$_2$ at position 2), 4.07, 4.87(d, d, 2H, J=14 Hz, —CH$_2$S— at position 3), 4.35~4.53(m, 1H, H at position 2 of proline), 5.04(d, 1H, J=5 Hz, H at position 6), 5.15(s, 2H —CO$_2$CH$_2$—), 5.81(d×d, 1H, J=9 and 5 Hz, H at position 7), 7.42(m, 5H, phenyl), 9.3(br, 2H,

9.40(d, 1H, J=9 Hz, —CONH—).

1-Acetoxyethyl 7-[D-O-(glycyl)mandelamido]-3-[(5-methyl-1,3,4-thiadiazol-2-yl)thiomethyl]-3-cephem-4-carboxylate hydrochloride (Compound No. 8) [Example 11]

IR(nujol, cm$^{-1}$); 1780, 1760, 1685.

NMR((CD$_3$)$_2$SO, δ values); 1.48, 1.50(d, d, 3H, J=6 Hz,

2.03, 2.07(s, s, 3H, —COCH$_3$), 2.68(s, 3H, thiadiazole —CH$_3$), 3.65(br, s, 2H, H$_2$ at position 2), 3.97(br, s, 2H, —OCOCH$_2$—), 4.13, 4.50(d, d, 2H, J=14 Hz, —CH$_2$S— at position 3), 5.07(d, 1H, J=5 Hz, H at position 6), 5.7(m, 1H, H at position 7), 6.12(s, 1H,

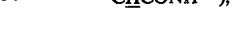

6.92, 7.01(q, q, 1H, J=6 Hz,

7.43(m, 5H, phenyl), 8.6(br, 3H, —NH$_3$+), 9.45(d, 1H, J=9 Hz, —CONH—).

1-Acetoxyethyl 7-[D-O-(L-α-aspartyl)mandelamido]-3-[(5-methyl-1,3,4-thiadiazol-2-yl)thiomethyl]-3-cephem-4-carboxylate hydrochloride (Compound No. 106) [Example 12]

IR(nujol, cm$^{-1}$); 1780, 1760, 1690.

NMR((CD$_3$)$_2$SO, δ values); 1.49, 1.52(d, d, 3H, J=7 Hz,

2.03, 2.07(s, s, 3H, —COCH$_3$), 3.05(d, 2H, J=6 Hz, —CH$_2$CO$_2$—), 2.70(s, 3H, thiadiazole —CH$_3$), 3.73(br. s, 2H, H$_2$ at position 2), 3.90~4.85(m, 3H,

—CH$_2$S—), 5.05, 5.07(d, d, 2H, J=5 Hz, H at position 6), 5.6(m, 1H, H at position 7), 6.09(s, 1H,

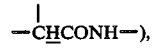

6.85, 6.98(q, q, 1H, J=7 Hz,

7.6(m, 6H, phenyl, —CO₂H), 8.7(br, s, 3H, —NH₃⁺), 9.48(d, 1H —CONH—).

1-Acetoxyethyl 7-[D-O-(L-glutaminyl)mandelamido]-3-[(5-methyl-1,3,4-thiadiazol-2-yl)thiomethyl]-3-cephem-4-carboxylate hydrochloride (Compound No. 78) [Example 13]

IR(nujol, cm⁻¹); 3100, 1785, 1720, 1690.

NMR((CD₃)₂SO, δ values); 1.46, 1.48(d, d, 3H, J=6 Hz,

2.03, 2.06(s, s, 3H, —COCH₃), 2.1∼2.65(m, 4H, —CH₂CH₂—), 2.66(s, 3H, thiadiazole —CH₃), 3.65(br, s, 2H, H₂ at position 2), 4.13, 4.51(d, d, 2H, J=14 Hz, —CH₂S— at position 3), 4.85(m, 1H,

5.07(d, 1H, J=5 Hz, H at position 6), 5.7(m, 1H, H at position 7), 6.1(s, 1H,

6.91, 7.1(q, q, 1H, J=7 Hz,

7.46(m, 5H, phenyl), 8.7(br, 5H, NH₃⁺, —CONH₂), 9.20(d, 1H, J=9 Hz, —CONH).

1-Acetoxyethyl 7-[D-O-(L-lysyl)mandelamido]-3-[(5-methyl-1,3,4-thiadiazol-2-yl)thiomethyl]-3-cephem-4-carboxylate 2 hydrochloride (Compound No. 134) [Example 14]

IR(nujol, cm⁻¹); 1780, 1750, 1680.

NMR((CD₃)₂SO, δ values); 1.2∼1.93(br, 6H, —(CH₂)₃—), 1.48, 1.50(d, d, 3H, J=6 Hz,

2.06, 2.08(s, s, 3H, —COCH₃), 2.68(s, 3H, thiadiazole —CH₃), 2.75(br, 2H,

—CH₂NH₃⁺), 4.03(m, 1H, —CH—NH₃⁺), 3.68(br, s, 2H, H₂ at position 2), 4.16; 4.56(d, d, 2H, J=14 Hz, —CH₂S— at position 3), 5.05(d, 1H, J=5 Hz, H at position 6), 5.75(m, 1H, H at position 7), 6.11(s, 1H,

6.94, 7.00(q, q, 1H, J=6 Hz,

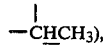

7.45(m, 5H, phenyl), 8.15(br, 3H, NH₃⁺), 8.83(br, 3H, NH₃⁺), 9.45(d, 1H, J=9 Hz, —CONH), 1-Acetoxyethyl 7-[D-O-(L-methionyl)mandelamido]-3-[(5-methyl-1,3,4-thiadiazol-2-yl)thiomethyl][-3-cephem-4-carboxylate hydrochloride] (Compound No. 162) [Example 15]

IR(nujol, cm⁻¹); 1780, 1750, 1685.

NMR((CD₃)₂SO, δ values); 1.47, 1.50(d, d, 3H, J=6 Hz,

2.01(s, 3H, CH₃S—), 2.04, 2.07(s, s, 3H, —COCH₃), 2.3(m, 4H, —CH₂CH₂—), 3.68(br, s, 2H, H₂ at position 2), 4.2∼4.62(m, 3H, —CH₂S— at position 3,

5.06(d, 1H, J=5 Hz, H at position 6), 5.8(m, 1H, H at position 7), 6.03 (s, 1H,

6.94, 7.04(q, q, 1H, J=4 Hz,

7.45(m, 5H, phenyl), 8.6(br, 3H, —NH₃⁺), 9.6(d, 1H, —CONH).

1-Acetoxyethyl 7-[D-O-(L-phenylalanyl)mandelamide]-3-[(5-methyl-1,3,4-thiadiazol-2-yl)thiomethyl]-3-cephem-4-carboxylate hydrochloride (Compound No. 92) [Example 16]

IR(nujol, cm⁻¹); 1780, 1755, 1685.

NMR((CD₃)₂SO, δ values); 1.48, 1.50(d, d, 3H, J=6 Hz,

2.03, 2.06(s, s, 3H, —COCH₃), 2.68(s, 3H, thiadiazole —CH₃), 3.22(d, 2H, J=7 Hz,

3.62(br, s, 2H, H₂ at position 2), 4.18, 4.66(d, d, 2H, J=14 Hz, —CH₂S— at position 3), 4.7(m, 1H,

5.06(d, 1H, J=5 Hz, H at position 6), 5.52~5.89(m, 1H, H at position 7), 6.06(s, 1H,

6.75~7.13(m, 1H,

7.21(s, 5H, phenyl), 7.37(s, 5H, phenyl), 8.84(br, 3H, —NH₃⁺), 9.42(d, 1H, J=9 Hz, —CONH—).

1-Acetoxyethyl 7-[D-O-(L-prolyl)mandelamido]-3-[(5-methyl-1,3,4-thiadiazol-2-yl)thiomethyl]-3-cephem-4-carboxylate hydrochloride (Compound No. 148) [Example 17]

IR (nujol, cm⁻¹); 1785, 1750, 1685.

NMR((CD₃)₂SO, δ values); 1.48, 1.50 (d, d, 3H, J=6 Hz,

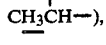

1.70, 2.40(m, 7H, H₂ at positions 3 and 4 of proline, CH₃CO—), 2.70(s, 3H, thiadiazole —CH₃), 3.05~3.45(m, 2H, H₂ at position 5 of proline), 3.64(br, s, 2H, H₂ at position 2), 4.10, 4.55(d, d, 2H, J=14 Hz, —CH₂S— at position 3), 4.35~4.53 (m, 1H, H at position 2 of proline), 5.04, 5.06(d, d, 1H, J=5 Hz, H at position 6), 5.85(m, 1H, H at position 7), 6.12 (s, 1H,

6.94, 7.00(q, q, 1H, J=6 Hz,

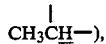

7.43 (m, 5H, phenyl), 9.30(br, 2H,

9.46(d, 1H, J=9 Hz, —CONH—).

1-Acetoxyethyl 7-[D-O-(β-alanyl)mandelamido]-3-[(5-methyl-1,3,4-thiadiazol-2-yl)thiomethyl]-3-cephem-4-carboxylate hydrochloride (Compound No. 190) [Example 18]

IR(nujol, cm⁻¹); 1785, 1765, 1690.

NMR((CD₃)₂SO, δ values); 1.46, 1.48(d, d, 3H, J=6 Hz,

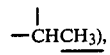

2.00, 2.04(s, s, 3H, —COCH₃), 2.35(t, 2H, J=6 Hz, —COCH₂—), 2.68(s, 3H, thiadiazole —CH₃), 3.1(m, 2H, —CH₂NH₃⁺), 3.65(br, s, 2H, H₂ at position 2), 4.12, 4.52(d, d, 1H, J=14 Hz, —CH₂S— at position 3), 4.15, 4.55(d, d, 1H, J=14 Hz, —CH₂S— at position 3), 5.09(d, 1H, J=5 Hz, H at position 6), 5.7 (d×d, 1H, J=9 and 5 Hz, H at position 7), 6.15(s, 1H,

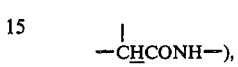

6.88, 6.96(q, q, 1H, J=6 Hz,

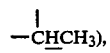

7.4 (m, 5H, phenyl), 8.73(br, 3H, —NH₃⁺), 9.46(d, 1H, J=9 Hz, —CONH—).

1-Acetoxyethyl 7-[D-O-(glycylglycyl)mandelamido]-3-[(5-methyl-1,3,4-thiadiazol-2-yl)thiomethyl]-3-cephem-4-carboxylate hydrochloride (Compound No. 204) [Example 19]

IR(nujol, cm⁻¹); 1780, 1760, 1680, 1630.

NMR((CD₃)₂SO, δ values); 1.50(d, 3H, J=5 Hz, —CHCH₃), 2.03, 2.06(s, s, 3H, —COCH₃), 2.68(s, 3H, thiadiazole —CH₃), 3.63(br, s, 4H, H₂ at position 2, —CH₂NH₃⁺), 3.85~4.2 (m, 4H, —CH₂S— at position 3), —CH₂NH—), 5.05(d, 1H, J=5 Hz, H at position 6), 5.52~5.93(m, 1H, H at position 7), 6.04(s, 1H,

6.92, 7.01(q, q, 1H, J=5 Hz,

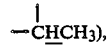

7.43(m, 5H, phenyl), 8.29(br, 3H, —NH₃⁺), 8.99 (br, 1H, —CH₂NH), 9.40(d, 1H, J=9 Hz, —CONH—).

1-Ethoxycarbonyloxyethyl 7-[D-O-(L-alanyl)mandelamido]-3-[(5-methyl-1,3,4-thiadiazol-2-yl)thiomethyl]-3-cephem-4-carboxylate hydrochloride (Compound No. 27) [Example 20]

IR(nujol, cm⁻¹); 1785, 1765, 1690.

NMR((CD₃)₂SO, δ values); 1.22(t, 3H, J=7 Hz, —CH₂CH₃), 1.48(d, 3H, J=7 Hz,

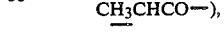

1.50(d, 3H, J=4 Hz,

2.68(s, 3H, thiadiazole —CH₃), 3.65(br, s, 2H, H₂ at position 2), 3.90~4.25(m, 5H, —CH₂S at position 3, —C$\underline{H}_2$CH₃,

5.06, 5.08(d, d, 1H, J=5 Hz, H at position 6), 5.55~5.93 (m, 1H, H at position 7), 6.12(s, 1H,

6.82, 6.90 (q, q, 1H, J=4 Hz,

7.45(m, 5H, phenyl), 8.68(br, 3H, —NH₃⁺), 9.46(d, 1H, J=9 Hz, —CONH—).

Phthalidyl 7-[D-O-(L-asparaginyl)mandelamido]-3-[(5-methyl-1,3,4-thiadiazol-2-yl)thiomethyl]-3-cephem-4-carboxylate hydrochloride (Compound No. 68) [Example 21]

IR(nujol, cm⁻¹); 1780, 1750, 1675, 1650
NNR((CD₃)₂SO, δ values); 2.90(d, 2H, J=6 Hz, —CH₂CO—), 2.70(s, 3H, thiadiazole —CH₃), 3.72(br, s, 2H, H₂ at position 2), 4.30(m, 1H,

4.20, 4.85(d, d, 2H, J=14 Hz, —CH₂S— at position 3), 5.15(d, 1H, J=5 Hz, H at position 6), 5.65(m, 1H, H at position 7), 6.14(s, 1H,

7.54(m, 8H, phenyl,

—CONH₂), 7.80(m, 4H, phthalidyl), 8.55 (br, s, 3H, —NH₃⁺), 9.45(d, 1H, J=9 Hz, —CONH—).

1-Acetoxyethyl 7-[D-O-(L-alanyl)mandelamido]-3-[1H-1,2,3-triazol-5-yl)thiomethyl]-3-cephem-4-carboxylate hydrochloride (Compound No. 380) [Example 22]

IR(nujol, cm⁻¹); 1785, 1760, 1685.
NMR((CD₃)₂SO, δ values); 1.50(d, 6H, J=6 Hz, 2×

2.05, 2.08(s, s, 3H, —COCH₃), 3.70(br, s, 2H, H₂ at position 2), 4.15, 4.55(d, d, 2H, J=14 Hz, —CH₂S— at position 3), 4.32(m, 1H,

5.05(d, 1H, J=5 Hz, H at position 6), 5.51(br, 1H, triazole —NH—), 5.75(m, 1H, H at position 7), 6.12(s, 1H,

6.92, 7.01(q, q, 1H, J=6 Hz,

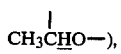

7.45(m, 5H, phenyl), 7.75(s, 1H, H at position 4 of triazole), 8.72(br, 3H, —NH₃⁺), 9.50(d, 1H, J=9 Hz, —CONH—).

1-Isobutyryloxyethyl 7-[D-O-(L-alanyl)mandelamido]-3-[(1,2,3-thiadiazol-5-yl)thiomethyl]-3-cephem-4-carboxylate hydrochloride (Compound No. 399) [Example 23]

IR(nujol, cm⁻¹); 3250, 1780, 1740, 1690.
NMR((CD₃)₂CO, δ values); 1.16(d, 6H, J=7 Hz, —(CH₃)₂), 1.46(d, 3H, J=8 Hz,

1.53, 1.56(d, d, 1H, J=6 Hz,

2.3~3.0(m, 1H, —C$\underline{H}$(CH₃)₂), 3.7(br, s, 2H, H₂ at position 2), 4.13~4.58(m, 3H, —CH₂S— at position 3,

5.1(d, 1H, J=5 Hz, H at position 6), 5.7(m, 1H, H at position 7), 6.05(s, 1H,

6.9, 7.15(q, q, 1H, J=6 Hz,

7.2~7.6(m, 5H, phenyl), 8.95(br, 3H, —NH₃⁺), 9.32(d, 1H, J=9 Hz, —CONH—), 9.57(s, 1H, H at position 4 of thiadiazole).

Pivaloyloxymethyl 7-[α-(L-alanyl)-p-hydroxymandelamido]-3-[(5-methyl-1,3,4-thiadiazol-2-yl)thiomethyl]-3-cephem-4-carboxylate hydrochloride (Compound No. 465) [Example 24]

IR(nujol, cm⁻¹); 3350, 1780, 1740, 1685.

NMR((CD₃)₂SO, δ values); 1.18, (s, 9H, —C(CH₃)₃), 1.46(d, 3H, J=7 Hz,

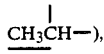

2.67(s, 3H, thiadiazole —CH₃), 3.65(br, s, 2H, H₂ at position 2), 4.25(m, 1H,

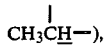

4.14, 4.60(d, d, 2H, J=14 Hz, —CH₂S— at position 3), 5.05 (d, 1H, J=5 Hz, H at position 6), 5.65~6.00(m, 4H, —CO₂CH₂—, H at position 7, —OH), 6.10(s, 1H,

6.75, 7.25(d, d, 4H, J=9 Hz, phenyl), 8.70(br, 3H, —NH₃⁺), 9.43(d, 1H, J=9 Hz, —CONH—).

1-Acetoxyethyl 7-[D-O-(L-alanyl)mandelamido]-3-caarbamoyloxymethyl-3-cephem-4-carboxylate hydrochloride (Compound No. 410) [Example 25]

IR(nujol, cm⁻¹); 1780, 1750, 1700, 1680.
NMR((CD₃)₂SO, 67 values); 1.48(d, 6H, J=7 Hz, 2×

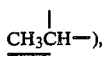

2.08(s, 3H, CH₃CO—), 3.60(br, s, 2H, H₂ at position 2), 4.25 (m, 1H,

4.65, 4.90(d, d, J=14 Hz, —CH₂O— at position 3), 5.08(d, 1H, J=5 Hz, H at position 6), 5.57~5.88(m, 1H, H at position 7), 6.10(s, 1H,

6.60(br, 2H, —CONH₂), 6.92, 7.00(q, q, 1H, J=7 Hz,

7.40(m, 5H, phenyl), 8.68(br, 3H, —NH₃⁺), 9.45(d, 1H, J=9 Hz, —CONH—).

1-Ethoxycarbonyloxyethyl 7-[D-O-(prolyl)mandelamido]-3-[(5-methyl-1,3,4-thiadiazol-2-yl)thiomethyl]-3-cephem-4-carboxylate hydrochloride (Compound No. 153) [Example 26]

IR (nujol, cm⁻¹); 1780, 1760, 1690.
NMR((CD₃)₂SO, δ values); 1.21(t, 3H, J=7 Hz, —CH₂CH₃), 1.53(d, 3H, J=5 Hz,

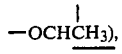

1.75~2.38(m, 4H, CH₂ at positions 3 and 4 of proline), 2.69(s, 3H, thiadiazole CH₃), 3.1~3.5 (m, 2H, CH₂ at position 5 of proline), 3.64(br, s, 2H, H₂ at position 2), 3.9~4.8(m, 5H, CH₂S at position 3, —CH₂CH₃, CH at position 2 of proline), 5.08(d, 1H, J=5 Hz, CH at position 6), 5.56~5.95(m, 1H, CH at position 7), 6.12(s, 1H,

6.88 (q, q, 1H, J=5 Hz,

7.58(br, s, 5H, phenyl), 9.5(d, 1H, J=9 Hz, —CONH), 8.5~10.8(br, 2H, —NH₂⁺).

Furthermore, by following the procedure of Example 2, there are also obtained the compounds described below in the Table 1. The compounds listed therein all have the D configuration with respect to the carbon atom marked with * in general formula (I), and are in the hydrochloride form.

The abbreviations used in said Table 1 respectively mean the following:

(1) In relation to R¹:
  Ala: alanyl
  β-Ala: β-alanyl
  Asn: asparaginyl
  α-Asp: α-aspartyl
  GlGl: glycylglycyl
  Gln: glutaminyl
  α-Glu: α-glutamyl
  Gly: glycyl
  Lys: lysyl
  Met: methionyl
  Phe: phenylalanyl
  Pro: prolyl
  Sar: sarcosyl
  Ser: seryl
  Val: valyl (2) In relation to R²:
  AOE: 1-acetoxyethyl  AOM: acetoxymethyl
  iBOE: 1-isobutyryloxyethyl
  nBOE: 1-n-butyryloxyethyl
  DOX: 5-methyl-1,3-dioxolen-2-on-4-ylmethyl
  ECE: 1-ethoxycarbonyloxyethyl
  PHT: phthalidyl  POE: 1-propionyloxyethyl
  POM propionyloxymethyl
  nVOE: 1-n-valeryloxyethyl
  iVOE: 1-isovaleryloxyethyl
  iVOM: isovaleryloxymethyl
  PVE: 1-pivaloyloxyethyl
  PVM: pivaloyloxymethyl (3) In relation to R³:
  CM: carbamoyloxymethyl
  MT: [(1-methyl-1H-tetrazol-5-yl)thiomethyl]
  MTD: [(5-methyl-1,3,4-thiadiazol-2-yl)thiomethyl]
  PD: [(3-hydroxypyridazin-6-yl)thiomethyl]
  TD: [(1,3,4-thiadiazol-2-yl)thiomethyl]

TR: [(1H-1,2,3-triazol-5-yl)thiomethyl]
TZ: [(1,2,3-thiadiazol-5-yl)thiomethyl]

TABLE 1

| Compound No. | R₁ | R₂ | R₃ | R₄ |
|---|---|---|---|---|
| 1 | Gly | AOM | MTD | H |
| 2 | Gly | POM | MTD | " |
| 3 | Gly | nBOE | MTD | " |
| 4 | Gly | iVOM | MTD | " |
| 5 | Gly | iBOE | MTD | " |
| 6 | Gly | nVOE | MTD | " |
| 7 | Gly | iVOE | MTD | " |
| 8 | Gly | AOE | MTD | " |
| 9 | Gly | POE | MTD | " |
| 10 | Gly | PVE | MTD | " |
| 11 | Gly | PVM | MTD | " |
| 12 | Gly | PHT | MTD | " |
| 13 | Gly | ECE | MTD | " |
| 14 | Gly | DOX | MTD | " |
| 15 | Ala | AOM | MTD | " |
| 16 | Ala | POM | MTD | " |
| 17 | Ala | nBOE | MTD | " |
| 18 | Ala | iVOM | MTD | " |
| 19 | Ala | iBOE | MTD | " |
| 20 | Ala | nVOE | MTD | " |
| 21 | Ala | iVOE | MTD | " |
| 22 | Ala | AOE | MTD | " |
| 23 | Ala | POE | MTD | " |
| 24 | Ala | PVE | MTD | " |
| 25 | Ala | PVM | MTD | " |
| 26 | Ala | PHT | MTD | " |
| 27 | Ala | ECE | MTD | " |
| 28 | Ala | DOX | MTD | " |
| 29 | Val | AOM | MTD | " |
| 30 | Val | POM | MTD | " |
| 31 | Val | nBOE | MTD | " |
| 32 | Val | iVOM | MTD | " |
| 33 | Val | iBOE | MTD | " |
| 34 | Val | nVOE | MTD | " |
| 35 | Val | iVOE | MTD | " |
| 36 | Val | AOE | MTD | " |
| 37 | Val | POE | MTD | " |
| 38 | Val | PVE | MTD | " |
| 39 | Val | PVM | MTD | " |
| 40 | Val | PHT | MTD | " |
| 41 | Val | ECE | MTD | " |
| 42 | Val | DOX | MTD | " |
| 43 | Ser | AOM | MTD | " |
| 44 | Ser | POM | MTD | " |
| 45 | Ser | nBOE | MTD | " |
| 46 | Ser | iVOM | MTD | " |
| 47 | Ser | iBOE | MTD | " |
| 48 | Ser | nVOE | MTD | " |
| 49 | Ser | iVOE | MTD | " |
| 50 | Ser | AOE | MTD | " |
| 51 | Ser | POE | MTD | " |
| 52 | Ser | PVE | MTD | " |
| 53 | Ser | PVM | MTD | " |
| 54 | Ser | PHT | MTD | " |
| 55 | Ser | ECE | MTD | " |
| 56 | Ser | DOX | MTD | " |
| 57 | Asn | AOM | MTD | " |
| 58 | Asn | POM | MTD | " |
| 59 | Asn | nBOE | MTD | " |
| 60 | Asn | iVOM | MTD | " |
| 61 | Asn | iBOE | MTD | " |
| 62 | Asn | nVOE | MTD | " |
| 63 | Asn | iVOE | MTD | " |
| 64 | Asn | AOE | MTD | " |
| 65 | Asn | POE | MTD | " |
| 66 | Asn | PVE | MTD | " |
| 67 | Asn | PVM | MTD | " |
| 68 | Asn | PHT | MTD | " |
| 69 | Asn | ECE | MTD | " |
| 70 | Asn | DOX | MTD | " |
| 71 | Gln | AOM | MTD | " |
| 72 | Gln | POM | MTD | " |
| 73 | Gln | nBOE | MTD | " |
| 74 | Gln | iVOM | MTD | " |
| 75 | Gln | iBOE | MTD | " |
| 76 | Gln | nVOE | MTD | " |
| 77 | Gln | iVOE | MTD | " |
| 78 | Gln | AOE | MTD | " |
| 79 | Gln | POE | MTD | " |
| 80 | Gln | PVE | MTD | " |
| 81 | Gln | PVM | MTD | " |
| 82 | Gln | PHT | MTD | " |
| 83 | Gln | ECE | MTD | " |
| 84 | Gln | DOX | MTD | " |
| 85 | Phe | AOM | MTD | " |
| 86 | Phe | POM | MTD | " |
| 87 | Phe | nBOE | MTD | " |
| 88 | Phe | iVOM | MTD | " |
| 89 | Phe | iBOE | MTD | " |
| 90 | Phe | nVOE | MTD | " |
| 91 | Phe | iVOE | MTD | " |
| 92 | Phe | AOE | MTD | " |
| 93 | Phe | POE | MTD | " |
| 94 | Phe | PVE | MTD | " |
| 95 | Phe | PVM | MTD | " |
| 96 | Phe | PHT | MTD | " |
| 97 | Phe | ECE | MTD | " |
| 98 | Phe | DOX | MTD | " |
| 99 | αAsp | AOM | MTD | " |
| 100 | αAsp | POM | MTD | " |
| 101 | αAsp | nBOE | MTD | " |
| 102 | αAsp | iVOM | MTD | " |
| 103 | αAsp | iBOE | MTD | " |
| 104 | αAsp | nVOE | MTD | " |
| 105 | αAsp | iVOE | MTD | " |
| 106 | αAsp | AOE | MTD | " |
| 107 | αAsp | POE | MTD | " |
| 108 | αAsp | PVE | MTD | " |
| 109 | αAsp | PVM | MTD | " |
| 110 | αAsp | PHT | MTD | " |
| 111 | αAsp | ECE | MTD | " |
| 112 | αAsp | DOX | MTD | " |
| 113 | αGlu | AOM | MTD | " |
| 114 | αGlu | POM | MTD | " |
| 115 | αGlu | nBOE | MTD | " |
| 116 | αGlu | iVOM | MTD | " |
| 117 | αGlu | iBOE | MTD | " |
| 118 | αGlu | nVOE | MTD | " |
| 119 | αGlu | iVOE | MTD | " |
| 120 | αGlu | AOE | MTD | " |
| 121 | αGlu | POE | MTD | " |
| 122 | αGlu | PVE | MTD | " |
| 123 | αGlu | PVM | MTD | " |
| 124 | αGlu | PHT | MTD | " |
| 125 | αGlu | ECE | MTD | " |
| 126 | αGlu | DOX | MTD | " |
| 127 | Lys | AOM | MTD | " |
| 128 | Lys | POM | MTD | " |
| 129 | Lys | nBOE | MTD | " |
| 130 | Lys | iVOM | MTD | " |
| 131 | Lys | iBOE | MTD | " |
| 132 | Lys | nVOE | MTD | " |
| 133 | Lys | iVOE | MTD | " |
| 134 | Lys | AOE | MTD | " |
| 135 | Lys | POE | MTD | " |
| 136 | Lys | PVE | MTD | " |
| 137 | Lys | PVM | MTD | " |
| 138 | Lys | PHT | MTD | " |
| 139 | Lys | ECE | MTD | " |
| 140 | Lys | DOX | MTD | " |
| 141 | Pro | AOM | MTD | " |
| 142 | Pro | POM | MTD | " |
| 143 | Pro | nBOE | MTD | " |
| 144 | Pro | iVOM | MTD | " |
| 145 | Pro | iBOE | MTD | " |
| 146 | Pro | nVOE | MTD | " |
| 147 | Pro | iVOE | MTD | " |
| 148 | Pro | AOE | MTD | " |
| 149 | Pro | POE | MTD | " |
| 150 | Pro | PVE | MTD | " |
| 151 | Pro | PVM | MTD | " |
| 152 | Pro | PHT | MTD | " |
| 153 | Pro | ECE | MTD | " |
| 154 | Pro | DOX | MTD | " |
| 155 | Met | AOM | MTD | " |
| 156 | Met | POM | MTD | " |
| 157 | Met | nBOE | MTD | " |
| 158 | Met | iVOM | MTD | " |
| 159 | Met | iBOE | MTD | " |

TABLE 1-continued

| Compound No. | R₁ | R₂ | R₃ | R₄ |
|---|---|---|---|---|
| 160 | Met | nVOE | MTD | " |
| 161 | Met | iVOE | MTD | " |
| 162 | Met | AOE | MTD | " |
| 163 | Met | POE | MTD | " |
| 164 | Met | PVE | MTD | " |
| 165 | Met | PVM | MTD | " |
| 166 | Met | PHT | MTD | " |
| 167 | Met | ECE | MTD | " |
| 168 | Met | DOX | MTD | " |
| 169 | Sar | AOM | MTD | " |
| 170 | Sar | POM | MTD | " |
| 171 | Sar | nBOE | MTD | " |
| 172 | Sar | iVOM | MTD | " |
| 173 | Sar | iBOE | MTD | " |
| 174 | Sar | nVOE | MTD | " |
| 175 | Sar | iVOE | MTD | " |
| 176 | Sar | AOE | MTD | " |
| 177 | Sar | POE | MTD | " |
| 178 | Sar | PVE | MTD | " |
| 179 | Sar | PVM | MTD | " |
| 180 | Sar | PHT | MTD | " |
| 181 | Sar | ECE | MTD | " |
| 182 | Sar | DOX | MTD | " |
| 183 | βAla | AOM | MTD | " |
| 184 | βAla | POM | MTD | " |
| 185 | βAla | nBOE | MTD | " |
| 186 | βAla | iVOM | MTD | " |
| 187 | βAla | iBOE | MTD | " |
| 188 | βAla | nVOE | MTD | " |
| 189 | βAla | iVOE | MTD | " |
| 190 | βAla | AOE | MTD | " |
| 191 | βAla | POE | MTD | " |
| 192 | βAla | PVE | MTD | " |
| 193 | βAla | PVM | MTD | " |
| 194 | βAla | PHT | MTD | " |
| 195 | βAla | ECE | MTD | " |
| 196 | βAla | DOX | MTD | " |
| 197 | GlGl | AOM | MTD | " |
| 198 | GlGl | POM | MTD | " |
| 199 | GlGl | nBOE | MTD | " |
| 200 | GlGl | iVOM | MTD | " |
| 201 | GlGl | iBOE | MTD | " |
| 202 | GlGl | nVOE | MTD | " |
| 203 | GlGl | iVOE | MTD | " |
| 204 | GlGl | AOE | MTD | " |
| 205 | GlGl | POE | MTD | " |
| 206 | GlGl | PVE | MTD | " |
| 207 | GlGl | PVM | MTD | " |
| 208 | GlGl | PHT | MTD | " |
| 209 | GlGl | ECE | MTD | " |
| 210 | GlGl | DOX | MTD | " |
| 211 | Gly | AOM | TD | " |
| 212 | Gly | POM | TD | " |
| 213 | Gly | nBOE | TD | " |
| 214 | Gly | iVOM | TD | " |
| 215 | Gly | iBOE | TD | " |
| 216 | Gly | nVOE | TD | " |
| 217 | Gly | iVOE | TD | " |
| 218 | Gly | AOE | TD | " |
| 219 | Gly | POE | TD | " |
| 220 | Gly | PVE | TD | " |
| 221 | Gly | PVM | TD | " |
| 222 | Gly | PHT | TD | " |
| 223 | Gly | ECE | TD | " |
| 224 | Gly | DOX | TD | " |
| 225 | Ala | AOM | TD | " |
| 226 | Ala | POM | TD | " |
| 227 | Ala | nBOE | TD | " |
| 228 | Ala | iVOM | TD | " |
| 229 | Ala | iBOE | TD | " |
| 230 | Ala | nVOE | TD | " |
| 231 | Ala | iVOE | TD | " |
| 232 | Ala | AOE | TD | " |
| 233 | Ala | POE | TD | " |
| 234 | Ala | PVE | TD | " |
| 235 | Ala | PVM | TD | " |
| 236 | Ala | PHT | TD | " |
| 237 | Ala | ECE | TD | " |
| 238 | Ala | DOX | TD | " |
| 239 | αAsp | AOM | TD | " |
| 240 | αAsp | POM | TD | " |
| 241 | αAsp | nBOE | TD | " |
| 242 | αAsp | iVOM | TD | " |
| 243 | αAsp | iBOE | TD | " |
| 244 | αAsp | nVOE | TD | " |
| 245 | αAsp | iVOE | TD | " |
| 246 | αAsp | AOE | TD | " |
| 247 | αAsp | POE | TD | " |
| 248 | αAsp | PVE | TD | " |
| 249 | αAsp | PVM | TD | " |
| 250 | αAsp | PHT | TD | " |
| 251 | αAsp | ECE | TD | " |
| 252 | αAsp | DOX | TD | " |
| 253 | Asn | AOM | TD | " |
| 254 | Asn | POM | TD | " |
| 255 | Asn | nBOE | TD | " |
| 256 | Asn | iVOM | TD | " |
| 257 | Asn | iBOE | TD | " |
| 258 | Asn | nVOE | TD | " |
| 259 | Asn | iVOE | TD | " |
| 260 | Asn | AOE | TD | " |
| 261 | Asn | POE | TD | " |
| 262 | Asn | PVE | TD | " |
| 263 | Asn | PVM | TD | " |
| 264 | Asn | PHT | TD | " |
| 265 | Asn | ECE | TD | " |
| 266 | Asn | DOX | TD | " |
| 267 | Phe | AOM | TD | " |
| 268 | Phe | POM | TD | " |
| 269 | Phe | nBOE | TD | " |
| 270 | Phe | iVOM | TD | " |
| 271 | Phe | iBOE | TD | " |
| 272 | Phe | nVOE | TD | " |
| 273 | Phe | iVOE | TD | " |
| 274 | Phe | AOE | TD | " |
| 275 | Phe | POE | TD | " |
| 276 | Phe | PVE | TD | " |
| 277 | Phe | PVM | TD | " |
| 278 | Phe | PHT | TD | " |
| 279 | Phe | ECE | TD | " |
| 280 | Phe | DOX | TD | " |
| 281 | Pro | AOM | TD | " |
| 282 | Pro | POM | TD | " |
| 283 | Pro | nBOE | TD | " |
| 284 | Pro | iVOM | TD | " |
| 285 | Pro | iBOE | TD | " |
| 286 | Pro | nVOE | TD | " |
| 287 | Pro | iVOE | TD | " |
| 288 | Pro | AOE | TD | " |
| 289 | Pro | POE | TD | " |
| 290 | Pro | PVE | TD | " |
| 291 | Pro | PVM | TD | " |
| 292 | Pro | PHT | TD | " |
| 293 | Pro | ECE | TD | " |
| 294 | Pro | DOX | TD | " |
| 295 | αGlu | AOM | TD | " |
| 296 | αGlu | POM | TD | " |
| 297 | αGlu | nBOE | TD | " |
| 298 | αGlu | iVOM | TD | " |
| 299 | αGlu | iBOE | TD | " |
| 300 | αGlu | nVOE | TD | " |
| 301 | αGlu | iVOE | TD | " |
| 302 | αGlu | AOE | TD | " |
| 303 | αGlu | POE | TD, | " |
| 304 | αGlu | PVE | TD | " |
| 305 | αGlu | PVM | TD | " |
| 306 | αGlu | PHT | TD | " |
| 307 | αGlu | ECE | TD | " |
| 308 | αGlu | DOX | TD | " |
| 309 | βAla | AOM | TD | " |
| 310 | βAla | POM | TD | " |
| 311 | βAla | nBOE | TD | " |
| 312 | βAla | iVOM | TD | " |
| 313 | βAla | iBOE | TD | " |
| 314 | βAla | nVOE | TD | " |
| 315 | βAla | iVOE | TD | " |
| 316 | βAla | AOE | TD | " |
| 317 | βAla | POE | TD | " |
| 318 | βAla | PVE | TD | " |
| 319 | βAla | PVM | TD | " |
| 320 | βAla | PHT | TD | " |
| 321 | βAla | ECE | TD | " |

TABLE 1-continued

| Compound No. | R₁ | R₂ | R₃ | R₄ |
|---|---|---|---|---|
| 322 | βAla | DOX | TD | " |
| 323 | Gly | AOM | MT | " |
| 324 | Gly | POM | MT | " |
| 325 | Gly | nBOE | MT | " |
| 326 | Gly | iVOM | MT | " |
| 327 | Gly | iBOE | MT | " |
| 328 | Gly | nVOE | MT | " |
| 329 | Gly | iVOE | MT | " |
| 330 | Gly | AOE | MT | " |
| 331 | Gly | POE | MT | " |
| 332 | Gly | PVE | MT | " |
| 333 | Gly | PVM | MT | " |
| 334 | Gly | PHT | MT | " |
| 335 | Gly | ECE | MT | " |
| 336 | Gly | DOX | MT | " |
| 337 | Ala | AOM | MT | " |
| 338 | Ala | POM | MT | " |
| 339 | Ala | nBOE | MT | " |
| 340 | Ala | iVOM | MT | " |
| 341 | Ala | iBOE | MT | " |
| 342 | Ala | nVOE | MT | " |
| 343 | Ala | iVOE | MT | " |
| 344 | Ala | AOE | MT | " |
| 345 | Ala | POE | MT | " |
| 346 | Ala | PVE | MT | " |
| 347 | Ala | PVM | MT | " |
| 348 | Ala | PHT | MT | " |
| 349 | Ala | ECE | MT | " |
| 350 | Ala | DOX | MT | " |
| 351 | αAsp | AOM | MT | " |
| 352 | αAsp | POM | MT | " |
| 353 | αAsp | nBOE | MT | " |
| 354 | αAsp | iVOM | MT | " |
| 355 | αAsp | iBOE | MT | " |
| 356 | αAsp | nVOE | MT | " |
| 357 | αAsp | iVOE | MT | " |
| 358 | αAsp | AOE | MT | " |
| 359 | αAsp | POE | MT | " |
| 360 | αAsp | PVE | MT | " |
| 361 | αAsp | PVM | MT | " |
| 362 | αAsp | PHT | MT | " |
| 363 | αAsp | ECE | MT | " |
| 364 | αAsp | DOX | MT | " |
| 365 | Pro | AOM | MT | " |
| 366 | Pro | POM | MT | " |
| 367 | Pro | nBOE | MY | " |
| 368 | Pro | iVOM | MT | " |
| 369 | Pro | iBOE | MT | " |
| 370 | Pro | nVOE | MT | " |
| 371 | Pro | iVOE | MT | " |
| 372 | Pro | AOE | MT | " |
| 373 | Pro | POE | MT | " |
| 374 | Pro | PVE | MT | " |
| 375 | Pro | PVM | MT | " |
| 376 | Pro | PHT | MT | " |
| 377 | Pro | ECE | MT | " |
| 378 | Pro | DOX | MT | " |
| 379 | Ala | POM | TR | " |
| 380 | Ala | AOE | TR | " |
| 381 | Ala | iBOE | TR | " |
| 382 | Ala | PHT | TR | " |
| 383 | Ala | ECE | TR | " |
| 384 | Ala | DOX | TR | " |
| 385 | Gly | POE | TR | " |
| 386 | Gly | AOE | TR | " |
| 387 | Gly | iBOE | TR | " |
| 388 | Gly | PHT | TR | " |
| 389 | Gly | ECE | TR | " |
| 390 | Gly | DOX | TR | " |
| 391 | Gly | POE | TZ | " |
| 392 | Gly | AOE | TZ | " |
| 393 | Gly | iBOE | TZ | " |
| 394 | Gly | PHT | TZ | " |
| 395 | Gly | ECE | TZ | " |
| 396 | Gly | DOX | TZ | " |
| 397 | Ala | POE | TZ | " |
| 398 | Ala | AOE | TZ | " |
| 399 | Ala | iBOE | TZ | " |
| 400 | Ala | PHT | TZ | " |
| 401 | Ala | ECE | TZ | " |
| 402 | Ala | DOX | TZ | " |
| 403 | Gly | POE | CM | " |
| 404 | Gly | AOE | CM | " |
| 405 | Gly | iVOE | CM | " |
| 406 | Gly | PHT | CM | " |
| 407 | Gly | ECE | CM | " |
| 408 | Gly | DOX | CM | " |
| 409 | Ala | POE | CM | " |
| 410 | Ala | AOE | CM | " |
| 411 | Ala | iBOE | CM | " |
| 412 | Ala | PHT | CM | " |
| 413 | Ala | ECE | CM | " |
| 414 | Ala | DOX | CM | " |
| 415 | Gly | AOE | PD | " |
| 416 | Gly | DOX | PD | " |
| 417 | Gly | ECE | PD | " |
| 418 | Gly | PHT | PD | " |
| 419 | Gly | PVM | PD | " |
| 420 | Ala | AOE | PD | " |
| 421 | Ala | DOX | PD | " |
| 422 | Ala | ECE | PD | " |
| 423 | Ala | PHT | PD | " |
| 424 | Ala | PVM | PD | " |
| 425 | Val | AOE | PD | " |
| 426 | Val | DOX | PD | " |
| 427 | Val | ECE | PD | " |
| 428 | Val | PHT | PD | " |
| 429 | Val | PVM | PD | " |
| 430 | Asm | AOE | PD | " |
| 431 | Asm | DOX | PD | " |
| 432 | Asm | ECE | PD | " |
| 433 | Asm | PHT | PD | " |
| 434 | Asm | PVM | PD | " |
| 435 | αAsp | AOE | PD | " |
| 436 | αAsp | DOX | PD | " |
| 437 | αAsp | ECE | PD | " |
| 438 | αAsp | PHT | PD | " |
| 439 | αAsp | PVM | PD | " |
| 440 | Lys | AOE | PD | " |
| 441 | Lys | DOX | PD | " |
| 442 | Lys | ECE | PD | " |
| 443 | Lys | PHT | PD | " |
| 444 | Lys | PVM | PD | " |
| 445 | Pro | AOE | PD | " |
| 446 | Pro | DOX | PD | " |
| 447 | Pro | ECE | PD | " |
| 448 | Pro | PHT | PD | " |
| 449 | Pro | PVM | PD | " |
| 450 | Gln | AOE | PD | " |
| 451 | Gln | DOX | PD | " |
| 452 | Gln | ECE | PD | " |
| 453 | Gln | PHT | PD | " |
| 454 | Gln | PVM | PD | " |
| 455 | αGl | AOE | PD | " |
| 456 | αGlu | DOX | PD | " |
| 457 | αGlu | ECE | PD | " |
| 458 | αGlu | PHT | PD | " |
| 459 | αGlu | PVM | PD | " |
| 460 | Lys | iBOE | PD | " |
| 461 | Gly | AOE | MTD | OH |
| 462 | Ala | POE | MTD | OH |
| 463 | Ala | AOE | MTD | OH |
| 464 | Ala | DOX | MTD | OH |
| 465 | Ala | PVM | MTD | OH |
| 466 | Ala | ECE | MTD | OH |

Physicochemical properties of Compounds listed in Table 1 are as follows:

Compound 11

IR(nujol, cm$^{-1}$); 3360~3180, 1780, 1760, 1690.
NMR((CD$_3$)$_2$SO, δ values); 1.16(s, 9H, —C(CH$_3$)$_3$), 2.68(s, 3H, thiadiazole, —CH$_3$), 3.63(br. s, 2H, —H$_2$ at position 2), 4.15, 4.54(d, d, 2H, J=14 Hz, —CH$_2$S— at position 3), 5.05(d, 1H, J=5 Hz, —H at position 6), 5.62—6.00(m, 3H, —H at position 7, —CO$_2$CH$_2$—), 6.13(s, 1H, —CH—OCO), 7.43(m, 5H, phenyl), 8.54(br, s, 3H, —NH$_3$⁺), 9.46(d, 1H, J=9 Hz, —CONH—).

Compound 13

IR(nujol, cm$^{-1}$); 1780, 1755, 1690.

NMR((CD$_3$)$_2$SO, δ values); 1.22(t, 3H, J=7 Hz, —CH$_2$CH$_3$), 1.53(d, 3H, J=6 Hz,

—OCHCH$_3$), 2.68(s, 3H, thiadiazole —CH$_3$), 3.64 (br. s, 2H, —H$_2$ at position 2), 3.8~4.7(m, 6H, —CH$_2$CH$_3$, —CH$_2$NH$_3^+$, —CH$_2$S— at position 3), 5.05(d, 1H, J=5 Hz, H at position 6), 5.5~5.91(m, 1H, —H at position 7), 6.13(s, 1H,

—CHCO), 6.8, 6.89(q, q, 1H, J=6.5 Hz,

—OCHCH$_3$), 7.15~7.78(m, 5H, phenyl), 8.3~9.1(br, 3H, —NH$_3^+$), 9.46(d, 1H, J=9 Hz, —CONH—).

Compound 14

IR(nujol, cm$^{-1}$); 1815, 1780, 1690

NMR((CD$_3$)$_2$SO, δ values); 2.18(s, 3H, dioxolene—CH$_3$), 2.70 (s, 3H, thiadiazole —CH$_3$), 3.65(br. s, 2H, —H$_2$ at position 2), 4.0(br. s, 2H, —OCOCH$_2$—), 4.05, 4.72(d, d, 2H, J=14 Hz, —CH$_2$S— at position 3), 5.04(d, 1H, J=5 Hz, —H at position 6), 5.15 (br. s, 2H, —CO$_2$CH$_2$—), 5.72(m, 1H, —H at position 7), 6.12 (s, 1H,

—CHCONH—), 7.43(m, 5H, phenyl), 8.75(br, 3H, —NH$_3^+$), 9.45(d, 1H, J=9 Hz, —CONH).

Compound 21

IR(nujol, cm$^{-1}$); 1780, 1750, 1685.

NMR((CD$_3$)$_2$SO, δ values); 0.9(d, 6H, J=6.5 Hz, —(CH$_3$)$_2$), 1.5(d, 6H, J=6.5 Hz,

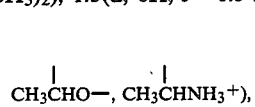
CH$_3$CHO—, CH$_3$CHNH$_3^+$), 1.7~2.2(m, 1H, —CH(CH$_3$)$_2$), 2.18(br. s, 2H, —CH$_2$CO$_2$—), 2.68(s, 3H, thiadiazole —CH$_3$), 3.84(br, s, 2H, —H$_2$ at position 2), 3.9~4.75(m, 3H,

—CHNH$_3^+$,

—CH$_2$S— at position 3), 5.06(d, 1H, J=5 Hz, —H at position 6), 5.53~5.91(m, 1H, —H at position 7), 6.13(s, 1H,

—CHCO—)

6.93, 7.02(q, q, 1H, J=6.5 Hz,

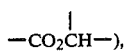
—CO$_2$CH—), 7.2~7.75(m, 5H, phenyl), 8.5~9.1(br, 3H, —NH$_3^+$), 9.46(d, 1H, J=9 Hz, —CONH).

Compound 24

IR(nujol, cm$^{-1}$); 1785, 1745, 1695.

NMR((CD$_3$)$_2$SO, δ values); 1.15(s, 9H, —C(CH$_3$)$_3$), 1.49(d, 6H, J=6 Hz, 2×

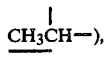
CH$_3$CH—), 2.68(s, 3H, thiadiazole —CH$_3$), 3.65(br. s, 2H, —H$_2$ at position 2), 3.85~4.75(m, 3H, —CH$_2$S— at position 3,

CH$_3$CHCO—), 5.08(d, 1H, J=5 Hz, —H at position 6), 5.55~5.95 (m, 1H, —H at position 7), 6.13(s, 1H,

—CHCONH—), 6.96, 7.05 (m, 1H,

—CH—CH$_3$), 7.44(m, 5H, phenyl), 8.75(br, 3H, —NH$_3^+$), 9.45(d, 1H, J=9 Hz, —CONH—).

Compound 26

IR(nujol, cm$^{-1}$); 3350, 1780, 1740, 1675.

NMR((CD$_3$)$_2$SO, δ values); 1.48(d, J=7 Hz, 3H,

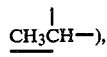
CH$_3$CH—), 2.66 (s, 3H, thiadiazole —CH$_3$), 3.68(br. s, 2H, —H$_2$ at position 2), 4.08~4.60(m, 3H, —CH$_2$S— at position 3,

—CHCH$_3$), 5.04(d, J=5 Hz, 1H, —H at position 6), 5.70(m, 1H, —H at position 7), 6.12(s, 1H,

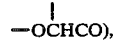
—OCHCO), 7.43(m, 5H, phenyl), 7.64(d, J=2 Hz, 1H,

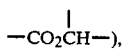

7.89(m, 4H, phtalide), 8.69(br. s, 3H, —NH$_3^+$), 9.47(m, 1H, —CONH—).

Compound 42

IR(nujol, cm$^{-1}$); 1815, 1780, 1680.
NMR((CD$_3$)$_2$SO, δ values); 0.97(d, J=7 Hz, 6H, (CH$_3$)$_2$), 2.17 (s, 3H, dioxolene —CH$_3$), 2.2(m, 1H, —C<u>H</u>(CH$_3$)$_2$), 2.67(s, 3H, thiadiazole —CH$_3$), 3.63(br, s, 2H, —H$_2$ at position 2), 4.0 (m, 1H,

4.11, 4.56(d, d, J=14 Hz, 2H, —CH$_2$S— at position 3), 5.04(d, J=5 Hz, 1H, —H at position 6), 5.16(s, 2H, —CO$_2$—CH$_2$—), 5.71(d, d, J=5 and 9 Hz, —H at position 7) 6.15(s, 1H,

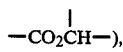

7.63(m, 5H, phenyl), 8.8(br, 3H, —NH$_3^+$), 9.4(d, J=9 Hz, —CONH—).

Compound 64

IR(nujol, cm$^{-1}$); 1780, 1755, 1675.
NMR((CD$_3$)$_2$SO, δ values); 1.50(d, 3H, J=6 Hz,

2.03, 2.05(s, s, 3H, —COCH$_3$), 2.69(s, 3H, thiadiazole —CH$_3$), 2.91(d, 2H, —C<u>H$_2$</u>—CO), 2.65(br. s, 2H, —H$_2$ at position 2), 3.90~4.65(m, 3H, —CH$_2$S— at position 3,

5.06(d, 1H, J=5 Hz, —H at position 6), 5.50~5.95(m, 1H, —H at position 7), 6.06(s, 1H,

6.89, 6.98(q, q, 1H, J=6 Hz,

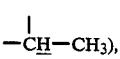

7.05~7.85(m, 7H, phenyl, —CONH$_2$), 8.57(br, 3H, —NH$_3^+$), 9.45(d, 1H, J=9 Hz, —CONH—).

Compound 69

IR(nujol, cm$^{-1}$); 1780, 1755, 1675.

NMR((CD$_3$)$_2$SO, δ values); 1.22(t, 3H, J=7 Hz, —CH$_2$CH$_3$), 1.53(d, 3H, J=6 Hz,

2.69(s, 3H, thiadiazole —CH$_3$), 2.91(d, 2H, —C<u>H$_2$</u>CO—), 3.66(br. s, 2H, —H$_2$ at position 2), 3.9~4.78(m, 3H, —CH$_2$S— at position 3,

5.06(d, 1H, J=5 Hz, —H at position 6), 5.51~5.94(m, 1H, —H at position 7), 6.10(s, 1H),

6.83, 6.90(q, q, 1H, J=6 Hz,

7.40(m, 5H, phenyl), 8.52(br, 3H, —NH$_3^+$), 9.46(d, 1H, J=9 Hz, —CONH—).

Compound 70

IR(nujol, cm$^{-1}$); 1815, 1780, 1675.
NMR((CD$_3$)$_2$SO, δ values); 2.16(s, 3H, dioxolene —CH$_3$), 2.70(s, 3H, thiadiazole —CH$_3$), 2.92(d, 2H, —CH$_2$CO—), 3.66 (br. s, 2H, —H$_2$ at position 2), 3.93~4.67(m, 3H, —CH$_2$S— at position 3,

5.04(d, 1H, J=5 Hz, —H at position 6), 5.17(br. s, 2H, —CO$_2$C<u>H$_2$</u>—), 5.72(m, 1H, —H at position 7), 6.10(s, 1H,

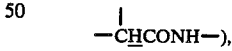

7.45(m, 5H, phenyl), 8.76(br. s, 3H, —NH$_3^+$), 9.46(d, 1H, J=9 Hz, —CONH—).

Compound 83

IR(nujol, cm$^{-1}$); 1780, 1755, 1670.
NMR((CD$_3$)$_2$SO, δ values); 1.23(t, 3H, J=7 Hz, —OCH$_2$—C<u>H$_3$</u>), 1.52(d, 3H, J=6 Hz,

2.25(m, 4H, —C$_2$H$_4$—), 2.68(s, 3H, thiadiazole —CH$_3$), 3.64(b. s, 2H, —H$_2$ at positio 2), 3.90~4.95(m, 5H, —OC<u>H$_2$</u>CH$_3$, —CH$_2$S— at position 3,

5.05 (d, 1H, J=5 Hz, —H at position 6), 5.55~5.93(m, 1H, —H at position 7), 6.43~7.28(m, 3H,

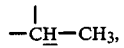

—CONH$_2$), 7.16~7.80 (m, 5H, phenyl), 8.82(br, 3H, —NH$_3^+$), 9.48(d, 1H, J=9 Hz, —CONH—).

Compound 84

IR(nujol, cm$^{-1}$); 1820, 1780, 1760, 1665.
NMR((CD$_3$)$_2$SO, δ values); 2.17(s, 3H, dioxolene —CH$_3$), 2.3 (m, 4H, —(CH$_2$)$_2$—), 2.67(s, 3H, thiadiazole —CH$_3$), 3.6(br, s, 2H, —H$_2$ at position 2), 3.9~4.8(m, 3H, —CH$_2$S— at position 3,

5.07(d, J=5 Hz, 1H, —H at position 6), 5.15(s, 2H, —CO$_2$CH$_2$—), 5.7~5.92(m, 1H, —H at position 7), 6.11(s, 1H

7.3(m, 7H —CONH$_2$, phenyl) 8.78(br. 3H, —NH$_3^+$), 9.40(d, J=9 Hz, 1H, —CONH—).

Compound 139

IR(nujol, cm$^{-1}$); 1780, 1755, 1680.
NMR ((CD$_3$)$_2$SO, δ values); 1.20~2.25(br, 6H, —(CH$_2$)$_3$—), 1.23(t, 3H, J=7 Hz, —CH$_2$CH$_3$), 1.54(d, 3H, J=6 Hz,

2.68(s, 3H, thiadiazole —CH$_3$), 2.70(br, 2H,

3.68 (br. s, 2H, —H$_2$ at position 2), 3.90~4.85(m, 5H, —CH$_2$S— at position 3, —CH$_2$CH$_3$,

5.07(d, 1H, J=5 Hz, —H at position 6), 5.67~5.93(m, 1H, —H at position 7), 6.16(s, 1H,

—CHCONH—), 6.83, 6.91(q, q, 1H, J=6 Hz,

7.46(m, 5H, phenyl), 8.15 (br, 3H, —NH$_3^+$), 8.81(br, 3H, —NH$_3^+$), 9.48(d, 1H, J=9 Hz, —CONH—).

Compound 140

IR(nujol, cm$^{-1}$); 1820, 1780, 1750, 1680.
NMR((CD$_3$)$_2$SO, δ values); 1.2~2.2(br, 6H, —(CH$_2$)$_3$—), 2.18 (s, 3H, dioxolene —CH$_3$), 2.67(s, 3H, thiadiazole —CH$_3$), 2.70 (br, 2H, —CH$_2$NH$_3^+$), 3.65(br. s, 2H, —H$_2$ at position 2), 4.0~4.7(m, 3H, —CH$_2$S— at position 3,

5.06(d, 1H, J=5 Hz, —H at position 6), 5.14(s, 2H, —CO$_2$CH$_2$—), 5.75(m, 1H, H at position 7), 6.12(s, 1H,

7.44(m, 5H, phenyl), 8.14(br, 3H, —NH$_3^+$), 8.78(br, 3H, —NH$_3^+$), 9.43(d, 1H, J=9 Hz, —CONH—).

Compound 150

IR(nujol, cm$^{-1}$); 1785, 1745, 1695.
NMR((CD$_3$)$_2$SO, δ values); 1.14(s, 9H, —C (CH$_3$)$_3$), 1.50(d, 3H, J=5 Hz,

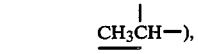

1.70~2.40(m, 4H, H$_2$ at position 3 and at position 4 of proline), 2.68(s, 3H, thiadiazole —CH$_3$), 3.1~3.5(m, 2H, —H$_2$ at position 5 of proline), 3.63(br. s, 2H, —H$_2$ at position 2), 4.0~4.75(m, 3H, —CH$_2$S— at position 3, —H at position 2 of proline), 5.06(d, 1H, J=5 Hz, —H at position 6), 5.55~5.90(m, 1H, —H at position 7), 6.12(s, 1H,

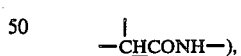

6.88, 6.96(q, q, 1H, J=5 Hz,

7.44(m, 5H, phenyl), 9.48(d, 1H, J=9 Hz, —CONH—), 9.0~10.0(br, 2H, —NH$_2^+$).

Compound 210

IR(nujol, cm$^{-1}$); 1815, 1780, 1760, 1670, 1630.
NMR((CD$_3$)$_2$SO, δ vlues); 2.18(s, 3H, dioxolene —CH$_3$) 2.68(s, 3H, thiadiazole —CH$_3$) 3.62(br, 4H, —H$_2$ at position 2, —CH$_2$NH$_3^+$) 3.8~4.1(m, 4H, —CH$_2$S— at position 3, —CH$_2$NH—) 5.04 (d, J=5 Hz, 1H, —H at position 6), 5.15(s, 2H, —CO$_2$—CH$_2$—), 5.52~5.9(m, 1H, —H at position 7), 6.02(s, 1H, —CO₂-CH—), 7.4(m, 5H, phenyl), 8.91(br, 4H, —CH₂NH, —NH₃⁺), 9.38(d, J=9 Hz, —CONH—).

Compound 330

IR(nujol, cm⁻¹); 1780, 1750, 1690.
NMR((CD₃)₂SO, δ values); 1.48, 1.50(d, d, 3H, J=6 Hz,

2.03, 2.07(s, s, 3H, —COCH₃), 3.65(br. s, 2H, —H₂ at position 2), 3.97(m, 5H, tetrazole —CH₃, —CH₂CO—), 4.15, 4.42(d, d, 2H, J=14 Hz, CH₂S— at position 3), 5.02(d, 1H, J=5 Hz, —H at position 6), 5.6(m, 1H, —H at position 7), 6.13(s, 1H,

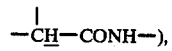

6.92, 7.01(q, q, 1H, J=6 Hz,

7.43(m, 5H, phenyl), 8.55(br, 3H, —NH₃⁺), 9.45(d, 1H, J=9 Hz, —CONH—).

Compound 332

IR(nujol, cm⁻¹); 1780, 1740, 1690.
NMR((CD₃)₂SO, δ values); 1.15(s, 9H, —C(CH₃)₃), 1.50(d, 3H, J=6 Hz,

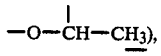

3.66(br. s, 2H, —H₂ at position 2), 3.70~4.75(m, 7H, tetrazole —CH₃, —CH₂CO—, —CH₂S— at position 3), 4.9~5.25(m, 1H, —H at position 6), 5.5~5.9(m, 1H, —H at position 7), 6.13(s, 1H,

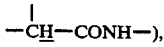

6.65~7.10(m, 1H,

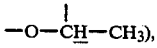

7.44(m, 5H, phenyl), 8.75(br, 3H, —NH₃⁺), 9.45(d, 1H, J=9 Hz, —CONH—).

Compound 335

IR(nujol, cm⁻¹); 1780, 1760, 1690.
NMR((CD₃)₂SO, δ values); 1.21(t, 3H, J=7 Hz, —CH₂CH₃), 1.53(d, 3H, J=6 Hz,

3.64(br. s, 2H, H₂ at postion 2), 3.90~4.90(m, 9H, tetrazole —CH₃, —CH₂CO—, —CH₂S— at position 3, —CH₂CH₃), 5.01(d, 1H, J=5 Hz, —H at position 6), 5.65(m, 1H, —H at position 7), 6.12(s, 1H,

6.85(m, 1H,

7.40(m, 5H, phenyl), 8.68(br. 3H, —NH₃⁺), 9.46(d, 1H, J=9 Hz, —CONH—).

Compound 336

IR(nujol, cm⁻¹); 1815, 1780, 1690.
NMR((CD₃)₂SO, δ values); 2.18(s, 3H, dioxolene —CH₃), 3.64(br. s, 2H, —H₂ at position 2), 3.95(m, 5H, tetrazole —CH₃, —OCOCH₂—), 4.05, 4.72(d, d, 2H, J=14 Hz, —CH₂S— at position 3), 5.04(d, 1H, J=5 Hz, —H at position 6), 5.15(br. s, 2H, —CO₂CH₂—), 5.72(m, 1H, —H at postion 7), 6.12(s, 1H,

7.43(m, 5H phenyl), 8.75(br. 3H, —NH₃⁺), 9.45(d, 1H, J=9 Hz, —CONH—).

Compound 344

IR(nujol), cm⁻¹); 1780, 1755, 1690.
NMR((CD₃)₂SO, δ values); 1.49(d, 6H, J=6 Hz, 2×CH₃CH—), 2.09(s, 3H, CH₃CO—), 3.65(br. s, 2H, —H₂ at position 2), 3.92(s, 3H, tetrazole —CH₃), 4.0~4.8(m, 3H, —CH₂S— at position 3,

5.08(d, 1H, J=5 Hz, —H at position 6), 5.74(m, 1H, —H at position 7), 6.12(s, 1H,

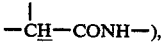

6.95(m, 1H, J=6 Hz,

7.45(m, 5H, phenyl), 8.7(br, 3H, —NH₃⁺), 9.45(d, 1H, J=9 Hz, —CONH—).

Compound 346

IR(nujol, cm⁻¹); 1780, 1740, 1690.
NMR((CD₃)₂SO, δ values); 1.14(s, 9H, —C(CH₃)₃), 1.44, 1.55 (d, d, 6H, J=6 Hz,

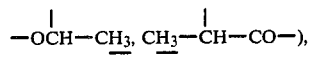

3.65(br. s, 2H, —H₂ at position 2), 3.75~4.7(m, 6H, tetrazole —CH₃, —CH₂S— at 3, $$CH_3-\underline{CH}-CO-),$$

4.9~5.2(m, 1H, —H at position 6), 5.5~5.9 (m, 1H, —H at position 7), 6.12(s, 1H, $$-\underline{CH}-CONH-),$$

6.65~7.10 (m, 1H,

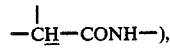

7.4(m, 5H, phenyl), 8.75(br, 3H, —NH₃⁺), 9.45(d, 1H, J=9 Hz, —CONH—).

Compound 347

IR(nujol, cm⁻¹); 1785, 1755, 1690.
NMR((CD₃)₂SO, δ values); 1.16(s, 9H, —C(CH₃)₃), 1.47(d, 3H, J=7 Hz, $$-\underline{CH}-CH_3),$$

3.64(br. s, 2H, —H₂ at position 2), 3.93 (s, 3H, tetrazole —CH₃), 4.0~4.7(m, 3H, —CH₂S— at position 3, $$-\underline{CH}-NH_3^+),$$

5.02(d, 1H, J=5 Hz, —H at position 6), 5.60~6.05 (m, 3H, —H at position 7, —CO₂CH₂—), 6.13(s, 1H, $$-\underline{CH}-CONH-)$$

7.42(m, 5H, phenyl), 8.63(br, 3H, —NH₃⁺), 9.45(d, 1H, J=9 Hz, —CONH—).

Compound 349

IR(nujol, cm⁻¹); 1785, 1765, 1690.
NMR((CD₃)₂SO, δ values); 1.22(t, 3H, J=7 Hz, —CH₂CH₃), 1.48(d, 3H, J=7 Hz, $$CH_3\underline{CH}CO-),$$

1.50(d, 3H, J=4 Hz, $$-O\underline{CH}CH_3),$$

3.65(br. s, 2H, —H₂ at position 2), 3.9~4.4(m, 8H, tetrazole —CH₃, —CH₂S— at position 3, —C<u>H</u>₂CH₃, —C<u>H</u>—NH₃⁺), 5.07(d, 1H, J=5 Hz, —H at position 6), 5.7(m, 1H, —H at position 7), 6.12 (s, 1H, $$-\underline{CH}CONH),$$

6.85(m, 1H, $$-O-\underline{CH}CH_3),$$

7.45(m, 5H, phenyl), 8.68(br, 3H, —NH₃⁺), 9.46(d, 1H, J=9 Hz, —CONH—).

Compound 350

IR(nujol, cm⁻¹); 1815, 1780, 1690.
NMR((CD₃)₂SO, δ values); 1.48(d, 3H, J=7 Hz, $$-\underline{CH}CH_3),$$

2.18 (s. 3H, dioxolene —CH₃), 3.62(br. s, 2H, —H₂ at position 2), 3.92(s, 3H, tetrazole —CH₃), 4.20(m, 1H, $$-\underline{CH}-NH_3^+),$$

4.07, 4.65 (d, d, 2H, J=14 Hz, —CH₂S— at position 3), 5.04(d, 1H, J=5 Hz, —H at position 6), 5.15(s, 2H, —CO₂CH₂—), 5.73(m, 1H, —H at position 7), 6.13(s, 1H, $$-\underline{CH}-CONH-),$$

7.4(m, 5H, phenyl), 8.73(br. 3H, —NH₃⁺), 9.46(d, 1H, J=9 Hz, —CONH—).

Compound 392

IR(nujol, cm⁻¹); 1780, 1760, 1690.
NMR((CD₃)₂SO, δ values); 1.48, 1.51(d, d, 3H, J=6 Hz, $$-CH_3\underline{CH}-),$$

2.04, 2.07(s, s, 3H, CH₃CO—), 3.66(br, 2H, —H₂ at position 2), 3.96(br. s, 2H, —CH₂CO—), 4.13, 4.50(d, d, 2H, J=14 Hz, —CH₂S— at position 3), 5.06(d, 1H, J=5 Hz, —H at position 6), 5.7(m, 1H, —H at position 7), 6.11(s, 1H,

—CH̲CO—), 6.92, 7.01(q, q, 1H, J=6 Hz,

—CH̲CH₃), 7.42(m, 5H, phenyl), 8.3(br, 3H, —NH₃⁺), 8.92 (s, 1H, thiadiazole —H), 9.49(d, 1H, J=9 Hz, —CONH—).

Compound 393

IR(nujol, cm⁻¹); 1780, 1750, 1690.
NMR((CD₃)₂SO, δ values); 1.15(d, 6H, J=7 Hz, —CH₃×2), 1.54, 1.56(d, d, 3H, J=6 Hz,

CH₃C̲HO—), 2.3~2.0(m, 1H, —C̲H(CH₃)₂), 3.68(br. s, 2H, —H₂ at position 2), 3.95(br. s, 2H, —CH₂CO—), 4.12, 4.50(d, d, 2H, J=14 Hz, —CH₂S— at position 3), 5.10(d, 1H, J=5 Hz, —H at position 6), 5.72(m, 1H, —H at position 7), 6.12(s, 1H,

—C̲HCONH—), 6.93, 7.01(q, q, 1H, J=6 Hz,

—C̲HCH₃), 7.45(m, 5H, phenyl), 8.92(s, 1H, thiadiazole —H), 9.5(m, 4H, —NH₃⁺, —CONH—).

Compound 395

IR(nujol, cm⁻¹); 1780, 1760, 1690.
NMR((CD₃)₂SO, δ values); 1.21(t, 3H, J=7 Hz, —CH₂CH₃), 1.53(d, 3H, J=6 Hz,

—OCHC̲H₃), 3.63(br, s, 2H, —H₂ at position 2), 3.7~4.8(m, 6H, —CH₂CH₃, —CH₂NH₃⁺, —CH₂S— at position 3), 5.06(d, 1H, J=5 Hz, —H at position 6), 5.45~5.92(m, 1H, —H at position 7), 6.13(s, 1H,

—C̲HCO—), 6.81, 6.88(q, q, 1H, J=6.5 Hz,

—OC̲HCH₃), 7.5(m, 5H, phenyl), 8.7(br, 3H, —NH₃⁺), 8.92(s, 1H, thiadiazole —H), 9.5(d, 1H, J=9 Hz, —CONH—).

Compound 396

IR(nujol, cm⁻¹); 1815, 1780, 1690.
NMR((CD₃)₂SO, δ values); 2.18(s, 3H, dioxolene —CH₃), 3.65(br. s, 2H, —H₂ at position 2), 4.0(br. s, 2H, —CH₂CO—), 4.04, 4.73(d, d, 2H, J=14 Hz, —CH₂S— at position 3), 5.05(d, 1H, J=5 Hz, —H at position 6), 5.15(br. s, 2H, —CO₂CH₂—), 5.72(m, 1H, —H at position 7), 6.12(s, 1H,

—C̲HCONH), 7.45(m, 5H, phenyl), 8.9 (br, 3H, —NH₃⁺), 8.9(s, 1H, thiadiazole —H), 9.5(d, 1H, J=9 Hz, —CONH—).

Compound 398

IR(nujol, cm⁻¹); 1780, 1755, 1685.
NMR((CD₃)₂SO, δ values); 1.48(d, 3H, J=7 Hz,

CH₃C̲HCO—), 1.48, 1.50(d, d, 3H, J=6 Hz,

CH₃C̲HO—), 2.05, 2.09(s, s, 3H, C₃CO—), 3.65(br, s, 2H, —H₂ at position 2), 4.14, 4.54(d, d, 2H, J=14 Hz, —CH₂S— at position 3), 4.81(m, 1H,

CH₃C̲H—), 5.08(d, 1H, J=5 Hz, —H at position 6), 5.75(m, 1H, —H at position 7), 6.11(s, 1H,

—C̲HCO—), 6.93, 7.02(q, q, 1H, J=6 Hz,

CH₃C̲HO—), 7.43(m, 5H, phenyl), 8.8(br, 3H, —NH₃⁺), 8.93(s, 1H, thiadiazole —H), 9.51(d, 1H, J=9 Hz, —CONH—).

Compound 401

IR(nujol, cm⁻¹); 1785, 1765, 1690.
NMR((CD₃)₂SO, δ values); 1.21(t, 3H, J=7 Hz, —CH₂CH₃), 1.46 (d, 3H, J=7 Hz,

CH₃C̲HCO—), 1.51(d, 3H, J=4 Hz,

—OCHCH₃), 3.64(br, s, 2H, —H₂ at position 2), 3.9~4.3(m, 5H, —CH₂CH₃, CH₂S— at position 3,

—CHNH₃⁺), 5.06, 5.08(d, d, 1H, J=5 Hz, —H at position 6), 5.7(m, 1H, —H at position 7), 6.1(s, 1H,

—CHCONH—), 6.82, 6.91(q, q, 1H, J=4 Hz,

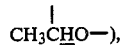
CH₃CHO—), 7.46(m, 5H, phenyl), 8.7 (br, 3H, —NH₃⁺), 8.92(s, 1H, thiadiazole —H), 9.56(d, 1H, J=9 Hz, —CONH—).

Compound 402

IR(nujol, cm⁻¹); 1815, 1780, 1690.
NMR((CD₃)₂SO, δ values); 1.48(d, 3H, J=7 Hz,

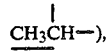
CH₃CH—), 2.17 (s, 3H, dioxolene —CH₃), 3.63(br. s, 2H, —H₂ at position 2), 4.2(m, 1H,

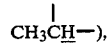
CH₃CH—), 4.06, 4.64(d, d, 2H, J=14 Hz, —CH₂S— at position 3), 5.06(d, 1H, J=5 Hz, —H at position 6), 5.15(s, 2H, —CO₂—CH₂—), 5.72(d, d, 1H, J=5 Hz, 9 Hz, —H at position 7), 6.13(s, 1H,

—CHCONH), 7.6(m, 5H, phenyl), 8.6(br, 3H, —NH₃⁺), 8.92(s, 1H, thiadiazole —H), 9.6(d, 1H, J=9 Hz, —CONH—).

Compound 464

IR(nujol, cm⁻¹); 1830, 1790, 1760, 1695, 1625.
NMR((CD₃)₂SO, δ values); 1.45(d, J=7 Hz, 3H,

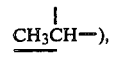
CH₃CH—), 2.18 (s, 3H, dioxolene —CH₃), 2.66(s, 3H, thiadiazole —CH₃), 3.64 (br, s, 2H, —H₂ at position 2), 4.08, 4.66(d, d, J=13 Hz, 2H, —CH₂S— at position 3), 4.00~4.3(m, 1H,

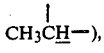
CH₃CH—), 5.12(d, J=5.5 Hz, 1H, —H at position 6), 5.63, 5.75(d, d, J=5.5 Hz, 9 Hz, 1H, —H at position 7), 6.00(s, 1H,

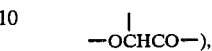
—OCHCO—), 6.78, 7.31(d, d, J=8.5 Hz, 4H, phenyl), 8.70(br, 4H, —OH, —NH₃⁺), 9.30(d, J=9 Hz, 1H, —CONH—).

Compound 466

IR(nujol, cm⁻¹); 1785, 1760, 1690, 1615.
NMR((CD₃)₂SO, δ values); 1.21(t, 3H, J=7 Hz, —CH₂CH₃), 1.45 (d, 3H, J=7 Hz,

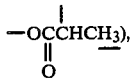
—OCCHCH₃),
  ‖
  O 1.51, 1.53(d, d, 3H, J=5 Hz,

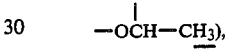
—OCH—CH₃), 2.68(s, 3H, thiadiazole —CH₃), 3.65(br. s, 2H, —H₂ at position 2), 3.97, 4.09, 4.50, 4.55(d.d, d.d, 2H, J=13 Hz, —CH₂S— at position 3), 4.17(q, 2H, J=7 Hz, —CH₂CH₃), 4.0~4.30(m, 1H,

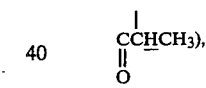
CCHCH₃),
‖
O 5.06, 5.08 (d, d, 1H, J=5.5 Hz, —H at position 6), 5.60~5.90(m, 1H, —H at position 7), 5.99(s, 1H,

—OCHCO—), 6.80, 6.88(q, q, 1H, J=5 Hz,

| Compound of Example 1 | 125 mg potency |
| Polyvinylpyrrolidone | 20 mg |
| Starch | 20 mg |
| Magnesium stearate | 2.0 mg |

6.78, 7.31(d, d, 4H, J=8.5 Hz, phenyl), 8.65(br, 4H, —OH, —NH₃⁺), 9.31(d, 1H, J=9 Hz, —CONH—).

DOSAGE FORM EXAMPLE 1

Tablets each having the composition given below are produced by the conventional method.

—OCHCH₃),

DOSAGE FORM EXAMPLE 2

Tablets each having the composition given below are produced by the conventional method.

| Compound of Example 2 | 250 mg potency |
|---|---|
| Citric acid | 50 mg |
| Starch | 20 mg |
| Magnesium stearate | 3.0 mg |

DOSAGE FORM EXAMPLE 3

Tablets each having the composition given below are produced by the conventional method.

| Compound of Example 3 | 500 mg potency |
|---|---|
| Starch | 20 mg |
| Hydroxypropylcellulose | 3 mg |
| Magnesium stearate | 5 mg |

DOSAGE FORM EXAMPLE 4

The compound of Example 2 and tartaric acid are admixed and capsules are filled therewith in the conventional manner. Each capsule contains the following:

| Compound of Example 2 | 125 mg potency |
|---|---|
| Tartaric acid | 25 mg |
| Magnesium stearate | 1 mg |
| Starch | To make 300 mg |

DOSAGE FORM EXAMPLE 5

Capsules each containing the ingredients given below are produced in the same manner as in Dosage Form Example 4.

| Compound of Example 1 | 125 mg potency |
|---|---|
| Magnesium stearate | 2 mg |
| Lactose | To make 200 mg |

DOSAGE FORM EXAMPLE 6

A dry syrup is produced according to the formulation given below.

| Compound of Example 2 | 62.5 mg potency |
|---|---|
| Citric acid | 25 mg |
| Sucrose | 70 mg |
| CMC-Na | 20 mg |

ACUTE TOXICITY TESTING

The results obtained in oral acute toxicity testing of the cephalosporin derivatives according to the present invention in mice are shown below.
Animals: Male mice (ICR, 5 weeks of age), n=3
Method of administration: The cephalosporin derivatives obtained in the above examples were dissolved in distilled water and the aqueous solutions were orally administered.
Results:

| Compound of | $LD_{50}$ (g/kg) |
|---|---|
| Example 1 | 5.0 |
| Example 7 | 5.0 |
| Example 9 | 5.0 |
| Example 17 | 5.0 |

ORAL ADMINISTRATION TEST

In humans, oral administration of the cephalosporin derivatives according to the present invention led to urinary recovery of the corresponding unesterified cephalosporins at the recovery rates shown below in the table.
Method of administration: A 125-mg (on the unesterified form basis) capsule was orally administered.
Assay: Microbial method using *Bacillus subtilis*
Results:

| Compound of | Percent urinary recovery (Hour 0 to Hour 8) |
|---|---|
| Example 1 | 38.0 |
| Example 2 | 35.2 |
| Example 3 | 37.0 |
| Example 6 | 36.0 |
| Example 7 | 41.0 |
| Example 9 | 41.0 |
| Example 17 | 40.9 |

What is claimed is:

1. A pharmacologically-acceptable antibacterial compound of the formula:

$$R^4-\text{C}_6H_4-\overset{*}{\text{CH}}(OR^1)-\text{CONH}-[\beta\text{-lactam-S ring}]-R^3, COOR^2 \quad (I)$$

wherein
$R^1$ is an α-, β- or γ-amino acid moiety (bonded by the ester linkage), which is optionally substituted by one or two lower alkyl groups at the amino group thereof,
$R^2$ is a 1-alkanoyloxyalkyl, 1-alkoxycarbonyloxyalkyl, phthalidyl or 5-methyl-1,3-dioxolen-2-on-4-ylmethyl group,
$R^3$ is a carbamoyloxymethyl group, which is optionally substituted by one or two lower alkyl groups, or a heterocyclothiomethyl group, which is optionally substituted by one or more members selected from the group consisting of alkyl having from 1 to 6 carbon atoms, cycloalkyl having 5 or 6 ring carbon atoms, alkenyl having from 2 to 4 carbon atoms, phenyl, tolyl, halo, hydroxy and amino; the heterocycle of the heterocyclothiomethyl group being pyrrolyl, pyrrolinyl, imidazolyl, pyrazolyl, pyridyl or an N-oxide thereof, pyrimidyl, pyrazinyl, pyridazinyl, triazolyl, tetrazolyl, pyrrolidinyl, imidazolidinyl, piperidino, piperazinyl, indolyl, isoindolyl, indolidinyl, benzimidazolyl, quinolyl, isoquinolyl, indazolyl, benzotriazolyl, oxazolyl, isoxazolyl, oxadiazolyl, morpholinyl, benzoxazolyl, benzoxadiazolyl, thiazolyl, thiadiazolyl, thiazolidinyl, thienyl, benzothiazolyl, benzothiadiazolyl or dihydrooxo-as-triazinyl; and $R^4$ is a hydrogen atom or a hydroxy group; or a non-toxic salt thereof.

2. A compound according to claim 1, wherein $R^1$ is glycyl, alanyl, valyl, prolyl, α-aspartyl or lysyl; or a non-toxic salt thereof.

3. A compound according to claim 1, wherein $R^2$ is 1-acetoxyethyl, 5-methyl-1,3-dioxolen-2-on-4-ylmethyl, 1-isobutyryloxyethyl, 1-pivaloyloxyethyl or 1-ethoxycarbonyloxyethyl; or a non-toxic salt thereof.

4. A compound according to claim 1 or a non-toxic salt thereof wherein $R^3$ is (5-methyl-1,3,4-thiadiazol-2-yl)thiomethyl or (1,3,4-thiadiazol-2-yl)thiomethyl.

5. A compound according to one of claims 1 to 4 which is in the D configuration with respect to the carbon atom marked with an asterisk (*) in the general formula (I), or a non-toxic salt thereof.

6. The compound of claim 1:
(5-methyl-1,3-dioxolen-2-on-4-methyl) 7-[D-O-(L-alanyl)mandelamido]-3-[(5-methyl-1,3,4-thiadiazole-2-yl)thiomethyl]-3-cephem-4-carboxylate hydrochloride.

7. The compound of claim 1:
(5-methyl-1,3-dioxolen-2-on-4-ylmethyl) 7-[D-O-(L-prolyl)mandelamido]-3-[(5-methyl-1,3,4-thiadiazole-2-yl)thiomethyl]-3-cephem-4-carboxylate hydrochloride.

8. The compound of claim 1:
(5-methyl-1,3-dioxolen-2-on-4-ylmethyl) 7-[D-O-(L-alanyl)mandelamido]-3-[(1-methyl-1H-tetrazol-5-yl)thiomethyl]-3-cephem-4-carboxylate hydrochloride.

9. The compound of claim 1:
1-acetoxyethyl 7-[D-O-(L-alanyl)mandelamido]-3-[(5-methyl-1,3,4-thiadiazol-2-yl)thiomethyl]-3-cephem-4-carboxylate hydrochloride.

10. The compound of claim 1:
1-acetoxyethyl 7-[D-O-(L-prolyl)mandelamido]-3-[(5-methyl-1,3,4-thiadiazol-2-yl)thiomethyl]-3-cephem-4-carboxylate hydrochloride.

11. The compound of claim 1:
1-acetoxyethyl 7[D-O-(L-alanyl)mandelamido]-3-[(1-methyl-1H-tetrazol-5-yl)thiomethyl]-3-cephem-4-carboxylate hydrochloride.

12. The compound of claim 1:
1-ethoxycarbonyloxyethyl 7-[D-O-(L-alanyl)mandelamido]-3-[(5-methyl-1,3,4-thiadiazol-2-yl)thiomethyl]-3-cephem-4-carboxylate hydrochloride.

13. The compound of claim 1:
1-ethoxycarbonyloxyethyl 7-[D-O-(L-prolyl)mandelamido]-3-[(5-methyl-1,3,4-thiadiazol-2-yl)thiomethyl]-3-cephem-4-carboxylate hydrochloride.

14. The compound of claim 1:
1-ethoxycarbonyloxyethyl 7-[D-O-(L-alanyl)mandelamido]-3-[(1-methyl-1H-tetrazol-5-yl)thiomethyl]-3-cephem-4-carboxylate hydrochloride.

15. The compound of claim 1:
(5-methyl-1,3-dioxolen-2-on-4-ylmethyl) 7-[D-O-glycylmandelamido]-3-[(5-methyl-1,3,4-thiadiazol-2-yl)thiomethyl]-3-cephem-4-carboxylate hydrochloride.

16. An orally administrable pharmaceutical composition useful for prevention or treatment of a bacterial infection and comprising, as an active ingredient, an antibacterially-effective amount of a compound of claim 1 or of a non-toxic salt thereof.

17. A compound according to claim 1 wherein $R^3$ is a carbamoyloxymethyl group which is optionally substituted by one or two lower alkyl groups.

18. A compound according to claim 1 wherein $R^3$ is a heterocyclothiomethyl group wherein the heterocycle is tetrazolyl, triazolyl, oxadiazolyl, thiadiazolyl or dihydro-oxo-as-triazinyl.

19. A compound according to claim 1 wherein $R^3$ is heterocyclothiomethyl wherein the heterocycle is tetrazolyl, thiadiazolyl or triazolyl.

20. A method for treating a bacterial infection which comprises orally administering to a warm-blooded animal afflicted with such an infection an antibacterially-effective amount of a compound according to claim 1.

* * * * *